(12) United States Patent
Cotten et al.

(10) Patent No.: US 6,284,880 B1
(45) Date of Patent: Sep. 4, 2001

(54) CHICKEN EMBRYO LETHAL ORPHAN (CELO) VIRUS GAM-1

(75) Inventors: Matthew Cotten; Adam Baker; Susanna Chiocca, all of Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 08/750,180

(22) PCT Filed: May 26, 1995

(86) PCT No.: PCT/EP95/01989

§ 371 Date: Feb. 14, 1997

§ 102(e) Date: Feb. 14, 1997

(87) PCT Pub. No.: WO95/33062

PCT Pub. Date: Dec. 7, 1995

(30) Foreign Application Priority Data

May 30, 1994 (DE) ................................................ 44 18 825
Nov. 30, 1994 (DE) ................................................ 44 42 587

(51) Int. Cl.$^7$ .............................. C07H 21/04; C07K 1/00; C12N 15/00; C12N 15/63
(52) U.S. Cl. ........................ 536/23.5; 530/350; 424/93.1; 424/93.2; 435/320.1; 435/455
(58) Field of Search ........................ 424/93.1; 435/320.1, 435/455; 514/44; 530/350; 536/23.1, 23.5

(56) References Cited

U.S. PATENT DOCUMENTS

| 5,354,844 | 10/1994 | Beug et al. | 530/345 |
| 5,521,291 | 5/1996 | Curiel et al. | 530/391.7 |
| 5,547,932 | 8/1996 | Curiel et al. | 435/65 |

FOREIGN PATENT DOCUMENTS

WO 93/07283    4/1993    (WO) .

OTHER PUBLICATIONS

McCoy et al. Expression of human interleukin–1 receptor antagonist in mouse lungs using a recombinant adenovirus: effects on vector–induced inflammation. Gene Therapy 2: 437–442, 1995.*
Simon et al. Adenovirus–mediated transfer of CFTR gene to lung or nonhuman primates: Toxicity study. Human Gene Therapy 4: 771–780, 1993.*
Clarke et al. Apoptosis in vivo and in vitro: conflict or complementarity? Molec. Med. Today (May 1996) pp. 189–191.*
Clarke et al. Thymocyte apoptosis induced by p53–dependent and independent pathways. Nature 362: 849–852, Apr. 1993.*
Friedmann, T. Overcoming the obstacles to gene therapy. Sci. Am. (Jun. 1997) pp. 96–101.*
Orkin and Motulsky Report and recommendations of the panel to assess the NIH investment in research on gene therapy, Dec. 1995.*
Verma et al. Gene therapy—Promises, problems, and prospects. Nature 389: 239–242, Sep. 1997.*
Chiocca et al. The complete DNA sequence and genomic organization of the avian adenovirus CELO. J. Virol. 70(5):2939–2949, May 1996.*
Akopian, T.A., et al., "Sequence of an Avian Adenovirus (CELO) DNA Fragment (11.2–19.2%)," EMBL Database Accession No. Z22864 (1993).
Chiou, S.–K., et al., "Functional Complementation of the Adenovirus E1B 19–Kilodalton Protein with Bcl–2 in the Inhibition of Apoptosis in Infected Cells," *J. Virol.* 68(10):6553–6566 (1994).
Curiel, D.T., et al., "High–Efficiency Gene Transfer Mediated by Adenovirus Coupled to DNA–Polylysine Complexes," *Human Gene Ther.* 3:147–154 (1992).
Debbas, M. and E. White, "Wild–type p53 mediates apoptosis by E1A, which is inhibited by E1B," *Gene & Dev.* 7:546–554 (1993).
Miyashita, T. and J.C. Reed, "bcl–2 Gene Transfer Increases Relative Resistance of S49.1 and WEHI7.2 Lymphoid Cells to Cell Death and DNA Fragmentation Induced by Glucocorticoids and Multiple Chemotheraeutic Drugs," *Can. Res.* 52:5407–5411 (1992).
Rao, L. et al., "The adenovirus E1A proteins induce apoptosis, which is inhibited by the E1B 19–kDa and Bcl–2 proteins," *Proc. Natl. Acad. Sci. USA* 89:7742–7746 (1992).
Zatloukal, K., et al., "Transferrinfection: A Highly Efficient Way to Express Gene Constructs in Eukaryotic Cells," *Ann. New York Acad. Sci.* 660:136–153 (1992).
International Search Report for PCT/EP95/01989 mailed Jun. 7, 1995.

* cited by examiner

Primary Examiner—Karen M. Hauda
Assistant Examiner—Anne-Marie Baker
(74) Attorney, Agent, or Firm—Sterne, Kessler, Goldstein & Fox PLLC

(57) ABSTRACT

The toxicity problems which occur when foreign material is introduced into higher eukaryotic cells, particularly during transfection with DNA, are countered by causing gene products to be expressed in the cell, which block the apoptosis triggered by the transfection process, and/or by treating the cells with anti-inflammatory substances. Preferably, Bcl-2, E1B 19K or an anti-apoptotically active gene of chicken adenovirus CELO is used as the anti-apoptosis gene whilst the inflammatory substance used is adenovirus VA1, which is introduced into the cell in the form of VA1-DNA. Using these methods, long-lasting gene expression can be achieved.

2 Claims, 21 Drawing Sheets

Figure 1A:
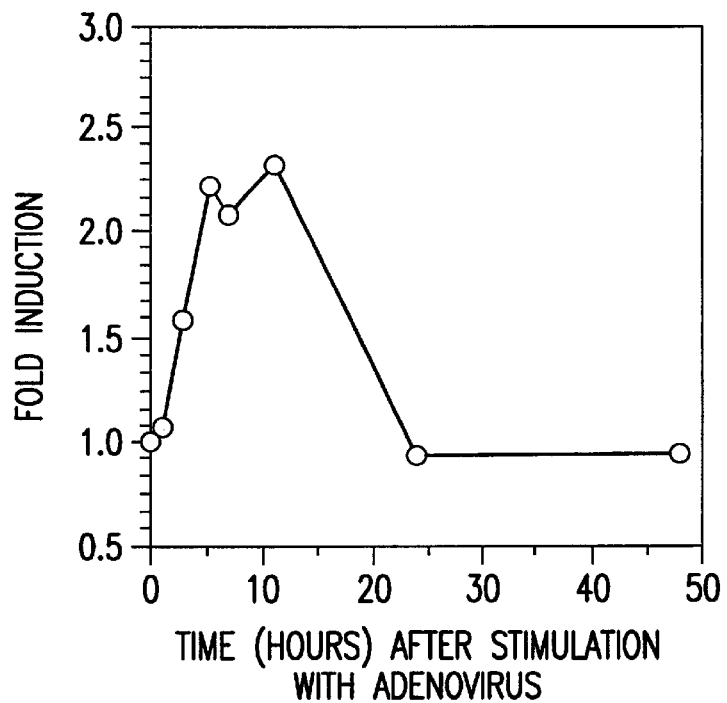

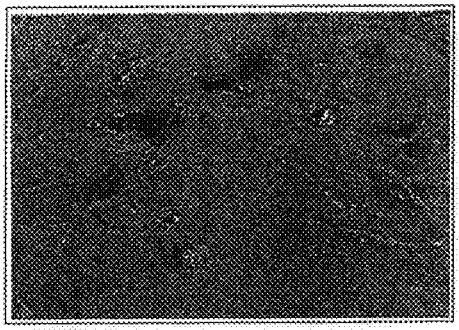 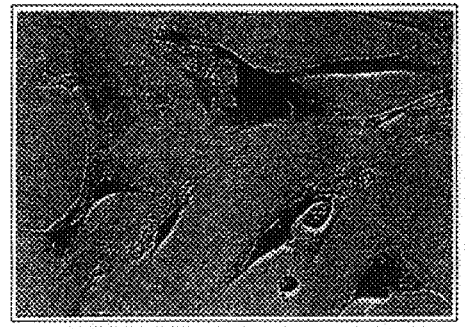
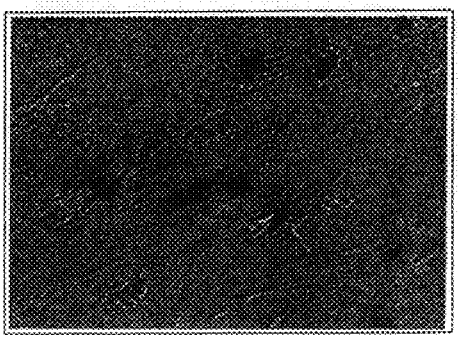 
Fig. 7

```
           10          20          30          40          50          60          70          80
   1 CCCGGGAACC TATTATTGAT TAACTAGACA GTACTTCCTC ATTTTCTACT GGAACTTTCC ACTGCCCTCC GGGGATTTTC   80
  81 CATTGGCAAT CATTAACTTG ACTTTGTACT TTATGTTTAC TCTCCATAGC AACGCACCTT ATATGGAAAA TATGCTCCTC  160
 161 CCCGGACCGC CCATCGTACC ACCTGAGCAG GTAGGCTGTA CCTTTTCCTA TTGGCCCATT ATGAGCTCAC CTGGTTAATC  240
 241 ATATACCCGC TCCGCCTATA TAGGTAGCAT ACCGGGACAG GTTCCCTCAC AGTCTATTGC AGACTGCCGA AGAGAGAGGA  320
 321 GCTCCGCATA GGACTGGGAC CAGAACCCCG AGACTCTGCC GGTAATATTT TAATTTCATT TAATCGAATC AAATAAATCA  400
 401 AAAATCAACT CAAACCATG ATCTCAATG GAAATTTCTT GTGATTTTCT TTCGCGCGCG ACCACCCCCT ATGGCACCCC  480
 481 CCTGTACACC CCCCCTGTA CAAGGGAACC TACCCCCCTG TACAGCGACC ACCCCCATG CTACATGGGG GACACCCCCC  560
 561 TGTACATTCT ACAGGTATGG CCCGCAACCC ATTCCGCATG TTCCCTGGGG ACCTTCCATA CCTTAGAGAAA TGGTGACCAC CGGCCTGATT  640
 641 TTACTTCGGT GGTCCCTGTG GACCCTAGCC AGCGGAATCC CACCACTAGC CTTAGAGAAA TGGTGACCAC CGGCCTGATT  720
 721 TTTAACCCTA ACCTGACCGG CGAGCAACTG CGGGAATACT CATTCAGCCC CCTAGTGTCC ATGGGAGAA AGGCAATCTT  800
 801 CGCAGACTAC GAGGGTCCCC AGCGCATTAT CCACGTTACC ATTAGGGGGC GCTCCGCGGA ACCCAAGACC CCCAGTGAGG  880
 881 CCCTCATTAT GATGGAGAAG GCGGTCCGTG GGCTTCCCCA GGTTCCTGAT TGGGTGGCCA GGGAATACTC GGATCCCCTC  960
 961 CCCACGGCA TAACCCACGT GGGGGACCTG CCCTGGCTAT TTGGTTCCGT GCATGCCCTG AAGATGGCGC TAGACACACT 1040
1041 GAAGATCCAT GTCCCTCGCG GAGTGGGGGT CCCTGGCTAT GAGGGTCTCT GTGGGACCAC CACCATCAAA GCCCCCGAC 1120
1121 AATATCGGCT CCTGACCACT GGAGTTTTCA CCAAAAAAGA TCTGAAAAGA ACACTTCCAG AACCATTCTT CAGCCGATTT 1200
1201 TTTAACCAAA CTCCCGAAGT TTGTGCCATC AAGACTGGCA AAAATCCGTT TTCTACAGAA ATTTGGTGTA TGACTCTCGG 1280
1281 CGGGATAGC CCCGCCCCG AGAGAAATGA ACCCAGAAAT CCCCATTCTC TCCAAGATTG GGCAAGACTG GGTGTCATGG 1360
1361 AAACCTGCCT AGTATGAGT AGGCGGGGAC TCGGGTCTCG GCACCACCCC TACCATTCTC TGTAACCAAT CCCTGAATAA 1440
1441 AGATTTGCAT AACAGAACTT TGACTCCTCC TTTTATGTGG GTGGGGTAAT GGGCGGCACT TGGGGTTCCT GGCGGTTCCT 1520
1521 ATTGGATGGG TAACACCGAC TCCGCCCTAC AAAGTTAATG ATTGATTTT CGGACTTAGA AAAATTTCGA CTGTCACCTG 1600
1601 GATGTTTTTC CCCACTTAAC CTCTAGGGGG AGATAGATCG CGTCCAAGGG GAGGAGCTCA ATACCGGACC GCCTATTAGG 1680
1681 TGTGGCTTCG GGCTCCGCCT AGTGGGAGGA GACAGGAAAA CCACGCCTAG TGACGCTGGG TCAAAGTCCA AGGGGAGTGG 1760
1761 TTTATGCGCA CCGGCCTTGGG GCGTGGTTTG GGCGGGGCAA GGTAACCCTT GGACTGGGAG GAGACTTCTG TCCCTTGGGC 1840
1841 GTGTCAAACA GGTAAACCCC ACCCGCGCGA TTAATGATTA ATTTTTCGGA CTTAGAAAAT TTTCAACCTG ATACTTTATT 1920
1921 TTCAAGCTT                                                                              1929
```

FIG. 14

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (vi) ORIGINAL SOURCE:
        (A) ORGANISM: Avian adenovirus
        (B) STRAIN: type 1

(viii) POSITION IN GENOME:
        (B) MAP POSITION: 33470-39676
        (C) UNITS: bp (ix) FEATURE:
        (A) NAME/KEY: 5'UTR
        (B) LOCATION: 1..576

(ix) FEATURE:
        (A) NAME/KEY: CDS
        (B) LOCATION: 577..1422

(ix) FEATURE:
        (A) NAME/KEY: 3'UTR
        (B) LOCATION: 1423..1929

(xi) SEQUENCE DESCRIPTION: SEQ ID NO:1:

CCCGGGAACC TATTATTGAT TAACTAGACA GTACTTCCTC ATTTTCTACT GGAACTTTCC          60

ACTGCCCTCC GGGGATTTTC CATTGGCAAT CATTAACTTG ACTTTGTACT TTATGTTTAC        120

TCTCCATAGC AACGCACCTT ATATGGAAAA TATGCTCCTC CCCGGACCGC CCATCGTACC        180
```

```
ACCTGAGCAG GTAGGCTGTA CCTTTTCCTA TTGGCCCATT ATGAGCTCAC CTGGTTAATC    240

ATATACCCGC TCCGCCTATA TAGGTAGCAT ACCGGGACAG GTTCCCTCAC AGTCTATTGC    300

AGACTGCCGA AGAGAGAGGA GCTCCGCATA GGACTGGGAC CAGAACCCCG AGACTCTGCC    360

GGTAATATTT TAATTTCATT TAATCGAATC AAATAAATCA AAAATCAACT CAAACCCATG    420

ATTCTCAATG GAAATTTCTT GTGATTTTCT TTCGCGCGCG ACCACCCCCT ATGGCACCCC    480

CCTGTACACC CCCCTGTACA CCCCCCTGTA CAAGGGAACC TACCCCCCTG TACAGCGACC    540

ACCCCCCATG GACACCCCCC TGTACATTCT ACAGGT ATG GCC CGC AAC CCA TTC      594
                                         Met Ala Arg Asn Pro Phe
                                          1               5

CGC ATG TTC CCT GGG GAC CTT CCA TAC TAC ATG GGG ACC ATT TCC TTT      642
Arg Met Phe Pro Gly Asp Leu Pro Tyr Tyr Met Gly Thr Ile Ser Phe
             10              15                  20

ACT TCG GTG GTC CCT GTG GAC CCT AGC CAG CGG AAT CCC ACC ACT AGC      690
Thr Ser Val Val Pro Val Asp Pro Ser Gln Arg Asn Pro Thr Thr Ser
             25              30                  35

CTT AGA GAA ATG GTG ACC ACC GGC CTG ATT TTT AAC CCT AAC CTG ACC      738
Leu Arg Glu Met Val Thr Thr Gly Leu Ile Phe Asn Pro Asn Leu Thr
     40              45                  50

GGC GAG CAA CTG CGG GAA TAC TCA TTC AGC CCC CTA GTG TCC ATG GGG      786
Gly Glu Gln Leu Arg Glu Tyr Ser Phe Ser Pro Leu Val Ser Met Gly
 55              60                  65                  70

AGA AAG GCA ATC TTC GCA GAC TAC GAG GGT CCC CAG CGC ATT ATC CAC      834
Arg Lys Ala Ile Phe Ala Asp Tyr Glu Gly Pro Gln Arg Ile Ile His
                 75              80                  85

GTT ACC ATT AGG GGG CGC TCC GCG GAA CCC AAG ACC CCC AGT GAG GCC      882
Val Thr Ile Arg Gly Arg Ser Ala Glu Pro Lys Thr Pro Ser Glu Ala
             90              95                  100

CTC ATT ATG ATG GAG AAG GCG GTC CGT GGC GCG TTC GCG GTT CCT GAT      930
Leu Ile Met Met Glu Lys Ala Val Arg Gly Ala Phe Ala Val Pro Asp
             105             110                 115

TGG GTG GCC AGG GAA TAC TCG GAT CCC CTC CCC CAC GGC ATA ACC CAC      978
Trp Val Ala Arg Glu Tyr Ser Asp Pro Leu Pro His Gly Ile Thr His
     120             125                 130

GTG GGG GAC CTG GGC TTC CCC ATT GGT TCC GTG CAT GCC CTG AAG ATG     1026
Val Gly Asp Leu Gly Phe Pro Ile Gly Ser Val His Ala Leu Lys Met
135             140                 145                 150

GCG CTA GAC ACA CTG AAG ATC CAT GTC CCT CGC GGA GTG GGG GTC CCT     1074
Ala Leu Asp Thr Leu Lys Ile His Val Pro Arg Gly Val Gly Val Pro
                 155             160                 165

GGC TAT GAG GGT CTC TGT GGG ACC ACC ACC ATC AAA GCC CCC CGA CAA     1122
Gly Tyr Glu Gly Leu Cys Gly Thr Thr Thr Ile Lys Ala Pro Arg Gln
             170             175                 180

TAT CGG CTC CTG ACC ACT GGA GTT TTC ACC AAA AAA GAT CTG AAA AGA     1170
Tyr Arg Leu Leu Thr Thr Gly Val Phe Thr Lys Lys Asp Leu Lys Arg
     185             190                 195

ACA CTT CCA GAA CCA TTC TTC AGC CGA TTT TTT AAC CAA ACT CCC GAA     1218
Thr Leu Pro Glu Pro Phe Phe Ser Arg Phe Phe Asn Gln Thr Pro Glu
 200             205                 210

GTT TGT GCC ATC AAG ACT GGC AAA AAT CCG TTT TCT ACA GAA ATT TGG     1266
Val Cys Ala Ile Lys Thr Gly Lys Asn Pro Phe Ser Thr Glu Ile Trp
215             220                 225                 230

TGT ATG ACT CTC GGC GGG GAT AGC CCC GCC CCC GAG AGA AAT GAA CCC     1314
Cys Met Thr Leu Gly Gly Asp Ser Pro Ala Pro Glu Arg Asn Glu Pro
                 235             240                 245

AGA AAT CCC CAT TCT CTC CAA GAT TGG GCA AGA CTG GGT GTC ATG GAA     1362
Arg Asn Pro His Ser Leu Gln Asp Trp Ala Arg Leu Gly Val Met Glu
```

```
                250                    255                    260
ACC TGC CTA CGT ATG AGT AGG CGG GGA CTC GGG TCT CGG CAC CAC CCC        1410
Thr Cys Leu Arg Met Ser Arg Arg Gly Leu Gly Ser Arg His His Pro
            265                    270                    275

TAC CAT TCT CTG TAA CCAATCCCTG AATAAAGATT TGCATAACAG AACTTTGACT        1465
Tyr His Ser Leu
        280

CCTCCTTTTA TGTGGGTGGG GTAATGGGCG GCACTTGGGG GTAATGGCGG TTCCTATTGG      1525

ATGGGTAACA CCGACTCCGC CCTACAAAGT TAATGATTGA TTTTTCGGAC TTAGAAAAAT      1585

TTCGACTGTC ACCTGGATGT TTTTCCCCAC TTAACCTCTA GGGGGAGATA GATCGCGTCC      1645

AAGGGGAGGA GCTCAATACC GGACCGCCTA TTAGGTGTGG CTTCGGGCTC CGCCTAGTGG      1705

GAGGAGACAG GAAAACCACG CCTAGTGACG CTGGGTCAAA GTCCAAGGGG AGTGGTTTAT      1765

GCGCACCGCC TTGGGGCGTG GTTTGGGCGG CGCAAGGTAA CCCTTGGACT GGGAGGAGAC      1825

TTCTGTCCCT TGGGCGTGTC AAACAGGTAA ACCCCACCCG CGCGATTAAT GATTAATTTT      1885

TCGGACTTAG AAAATTTTCA ACCTGATACT TTATTTTCAA GCTT                       1929
```

(2) INFORMATION FOR SEQ ID NO:2:

(i) SEQUENCE CHARACTERISTICS:
        (A) LENGTH: 282 amino acids
        (B) TYPE: amino acid
        (D) TOPOLOGY: linear (ii) MOLECULE TYPE: Protein (xi) SEQUENCE DESCRIPTION: SEQ ID NO:2:

```
Met Ala Arg Asn Pro Phe Arg Met Phe Pro Gly Asp Leu Pro Tyr Tyr
 1               5                  10                  15

Met Gly Thr Ile Ser Phe Thr Ser Val Val Pro Val Asp Pro Ser Gln
                20                  25                  30

Arg Asn Pro Thr Thr Ser Leu Arg Glu Met Val Thr Thr Gly Leu Ile
            35                  40                  45

Phe Asn Pro Asn Leu Thr Gly Glu Gln Leu Arg Glu Tyr Ser Phe Ser
        50                  55                  60

Pro Leu Val Ser Met Gly Arg Lys Ala Ile Phe Ala Asp Tyr Glu Gly
65                  70                  75                  80

Pro Gln Arg Ile Ile His Val Thr Ile Arg Gly Arg Ser Ala Glu Pro
                85                  90                  95

Lys Thr Pro Ser Glu Ala Leu Ile Met Met Glu Lys Ala Val Arg Gly
            100                 105                 110

Ala Phe Ala Val Pro Asp Trp Val Ala Arg Glu Tyr Ser Asp Pro Leu
        115                 120                 125

Pro His Gly Ile Thr His Val Gly Asp Leu Gly Phe Pro Ile Gly Ser
    130                 135                 140

Val His Ala Leu Lys Met Ala Leu Asp Thr Leu Lys Ile His Val Pro
145                 150                 155                 160

Arg Gly Val Gly Val Pro Gly Tyr Glu Gly Leu Cys Gly Thr Thr Thr
                165                 170                 175

Ile Lys Ala Pro Arg Gln Tyr Arg Leu Leu Thr Thr Gly Val Phe Thr
            180                 185                 190

Lys Lys Asp Leu Lys Arg Thr Leu Pro Glu Pro Phe Phe Ser Arg Phe
        195                 200                 205

Phe Asn Gln Thr Pro Glu Val Cys Ala Ile Lys Thr Gly Lys Asn Pro
    210                 215                 220
```

-continued

```
Phe Ser Thr Glu Ile Trp Cys Met Thr Leu Gly Gly Asp Ser Pro Ala
225                 230                 235                 240

Pro Glu Arg Asn Glu Pro Arg Asn Pro His Ser Leu Gln Asp Trp Ala
            245                 250                 255

Arg Leu Gly Val Met Glu Thr Cys Leu Arg Met Ser Arg Arg Gly Leu
            260                 265                 270

Gly Ser Arg His His Pro Tyr His Ser Leu
            275                 280
```

CHICKEN EMBRYO LETHAL ORPHAN (CELO) VIRUS GAM-1

The present invention relates to a method for treating higher eukaryotic cells, particularly for introducing foreign material such as DNA into the cells.

There is a need for an efficient system for introducing foreign material, particularly nucleic acid, into living cells especially in the field of gene therapy. This involves locking genes into cells in order to synthesise therapeutically active gene products in vivo.

Standard methods for the transfection of cells make use of, inter alia, calcium phosphate (for use in vitro), cationic lipids (Felgner et al., 1993) or liposomes.

The technologies which are currently most advanced in the field of gene therapy make use of recombinant vector systems (retroviruses or adenoviruses) for transferring genes into the cell (Wilson et al., 1990; Kasid et al., 1990, WO 93/03769).

Alternative strategies for gene transfer are based on mechanisms which the cell uses for transporting macromolecules. One example of this is the introduction of genes into the cell by the route of receptor-mediated endocytosis (e.g. Wu and Wu, 1987, Wagner et al., 1990, and EP-A1 0388 758).

Studies of gene therapy in general and non-viral gene transfer methods in particular are provided by Mulligan, 1993, and by Cotten and Wagner, 1993.

For gene transfer with DNA/polycation complexes by means of receptor-mediated endocytosis, an improvement has been proposed which envisages using components on the basis of their ability to release the contents of endosomes, e.g. adenoviruses or fusogenic peptides. The use of the endosomolytic components brings about an increase in the efficiency of gene transfer by avoiding the breakdown of the DNA complexes internalised in the cell in the lysosomes (Curiel et al., 1991; Curiel et al., 1992a; Zatloukal et al., 1992; Cotten et al., 1992; Wagner et al., 1992; Curiel et al., 1992b; WO 93/07283). It has been proposed, among other things, to modify the adenoviruses by binding to polylysine. The adenovirus-polylysine conjugates can be complexed with DNA, together with conjugates of transferrin-polylysine, to obtain ternary transferrin-polylysine/adenovirus-polylysine/DNA complexes (Wagner et al., 1992). The complexes bind to transferrin and adenovirus receptors on the target cells. After the endocytosis the adenovirus causes the endosomes to open up, resulting in the release of the material from the endosome into the cytoplasm. This technique, which is also known as "transferrinfection" is more reliable than conventional viral techniques (Cotten et al., 1992).

Admittedly, transiently high expression values have been achieved with adenovirus-aided gene transfer based on receptor-mediated endocytosis, but because of toxic effects in some types of cell it has not been possible to maintain expression over a longer period of time. These toxic effects can be traced back to various defence responses of the host cell, shortly after the virus enters the cell. The mechanisms which regulate the activation of these responses have not yet been explained. Investigations with replication-deficient adenovirus mutants lead one to suppose that the responses of the host occur very early on, possibly even before the expression of the virus gene.

One component of this host response is activation of the "Interferon Responsive Genes" (genes which respond to interferon), most probably by activation of ISGF3, a transcription factor which responds to interferon, the binding sites of which are found upstream of a series of genes responding to interferon. One of the activated genes is the protein kinase p68, which is activated by double-stranded RNA. p68 is synthesised in an inactive form and, in the presence of dsRNA is subject to autocatalytic phosphorylation which activates the kinase, leading to phosphorylation and inactivation of the translation initiation factor eIF2a, thereby blocking the initiation of protein translation. It has also been reported that NF-κB is activated by dsRNA (Visvanathan and Goodbourn, 1989), which indicates that perhaps p68 directly phosphorylates IκB and activates NF-κB.

The type C-adenoviruses have two powerful mechanisms for preventing this stoppage of translation by the host:

The E1A gene products can directly disrupt the activation of ISGF3 (Gutch and Reich, 1991; Ackrill et al., 1991).

A second, again directly acting mechanism makes use of the VA1-genes. The gene product forms a stable secondary structure which can bind to the p68 kinase without activating the kinase, and which can prevent binding and activation by the actual activators (Manche et al., 1992; Mathews and Shenk, 1991).

Another inflammatory reaction mechanism as a result of the entry of a virus would consist in the activation of the inflammatory transcription factor NF-IL-6 and the secretion of the inflammatory cytokine IL-6 (Sehgal et al., 1988; Kishimoto et al., 1992). This factor, often in collaboration with NF-κB, in turn activates the IL-6-gene itself as well as a number of inflammatory response genes such as TNF and IL-1. It has recently been reported that IL-6 can in turn activate the transcription factor IRF 1 ("Interferon Response Factor 1") which responds to interferon (Harroch et al., 1994). This would either be responsible for the interferon response to the entry of adenovirus or would intensify the response. Since the majority of the early genes of adenovirus type C contain binding sites for NF-IL-6, it may be assumed that activation of NF-IL-6 by adenovirus ensures that the virus gene expression cascade is triggered.

Another line of defence of the host cell would be the apoptotic response. It has long been known that mutations which map in the E1B 19K region are responsible for the deg-phenotype, an intensified cytopathic effect which is accompanied by the breakdown of the chromosomal DNA of the host (D'Halluin et al., 1979; Ezoe et al., 1981; Lai Fatt and Mak, 1982; Pilder et al., 1984; Subramanian et al., 1984; Takemori et al., 1984; White et al., 1984). Recent research has identified apoptosis which is caused by expression of an E1A growth signal in the absence of E1B (White and Stillman, 1987; White et al., 1994; Rao et al., 1992); the release of the transcription factor E2F from the Rb-protein, triggered by E1A, would appear to be involved in this apoptosis (Wu and Levine, 1994). It has been shown that the E1B 19K protein can function as a highly effective analogue of the host gene Bcl-2 which blocks the apoptosis (Rao et al., 1992; Debbas and White, 1993). The expression of each of these proteins may block an apoptosis triggered by various signals. In conjunction with the investigations with Myc, it has been found that growth signals determine a cell either for proliferation, if the appropriate reinforcing signals, e.g. Ras or Src, are available, or for apoptosis if only the Myc signals are available (Evan et al., 1992). A similar model for transformation induced by adenovirus E1 is supported by experiments which show that the apoptosis is triggered by E1A expression in the absence of E1B 19K (White and Stillman, 1987; Rao et al., 1992; Debbas and White, 1993). A recent investigation into the sindbis virus infection has shown that the expression of Bcl-2 in the host cell may be a critical factor in the outcome of a viral infection (Levine et al., 1993): in the absence of Bcl-2 the cell carries out apoptosis, thereby restricting the virus production to a short acute phase. In the presence of Bcl-2 expression, chronic virus production occurs because the apoptotic response to the acute phase infection is not achieved. Anti-apoptotic activities have also been identified in the Epstein-Barr virus (the BHER1 gene; Pearson et al., 1987), in the baculovirus (the p35 gene; Sugimoto et al., 1994) and in the African swine fever virus (the LMW5-HL gene; Neilan et al., 1993). This indicates that the apoptotic response to the virus infection occurs in many cases and viruses have developed strategies for blocking this response.

The experiments carried out with inactivated adenovirus capsids for gene transfer by means of receptor-mediated endocytosis were based first of all on the assumption that the virus capsid acts only as a reagent which opens up the endosomes, which is a function of the surface proteins of the virus capsid. Methods of inactivation have been developed which block the transcription and replication of the virus without affecting the endosomolytic activity of the capsid (Cotten et al., 1994). In the course of further experiments with adenovirus-aided transfections, contamination with lipopolysaccharide (LPS) was identified as a source of the toxicity in primary cell transfections. This toxicity problem could easily be remedied by the careful removal of LPS from the DNA. Although the inactivation of the virus and the removal of LPS eliminated two forms of virus-associated toxicity, long-term gene expression did not succeed in all cell types, even with psoralen/UV-inactivated human adenovirus in the presence of LPS-free DNA.

The aim of the present invention was to clarify the mechanisms which occur in the toxicity effects observed in transfections, in order to provide a new, improved method of treating eukaryotic cells, particularly for introducing foreign material, such as nucleic acids, into the cells, making use of the findings achieved.

Up till now, efforts to improve gene transfer methods have concentrated on increasing the gene expression. Thus, it has been reported, for example, that VA1 expression increases the gene expression of co-transfected genes by increasing the stability of mRNA or the quantity thereof (Svensson and Akusjarvi, 1984; Stijker et al., 1989; Svensson and Akusjarvi, 1990; Mathews and Shenk, 1991). The mechanism which is responsible for this has not yet been clarified at the molecular level; there would not appear to be any connection with toxicity problems.

The present invention relates to a process for treating higher eukaryotic cells, particularly for introducing foreign material such as nucleic acid into the cells, in which, apart from the foreign material and the transfection components:
   a) one or more nucleic acid molecules, particularly DNA molecules, are introduced into the cells, the expression products of which at least partially block the apoptosis of the host cell triggered by the introduction of the foreign material, and/or
   b) the inflammatory response of the cells is at least partially inhibited by
      i) treating the cells externally with one or more anti-inflammatory substances and/or
      ii) introducing into the cells one or more anti-inflammatory substances or the nucleic acid molecules, particularly DNA molecules, coding for them.

The DNA molecules defined in a) are hereinafter referred to as "anti-apoptosis genes" or as "DNA molecules with an anti-apoptosis effect".

In the process according to the invention, in its preferred embodiment, in addition to the components a) and optionally b) ii) the foreign material and the transfection components are introduced into the cells.

The definition of the term "apoptosis" within the scope of the present invention includes all toxic effects which can be put down to a) direct activation of the apoptotic response; b) activation of reactive oxygen metabolites which induce apoptosis directly or indirectly; c) activation of the secretion of TNF, IL-6 or another cytokine which affects the viability of the transduced cells; d) excess activation of NF-κB; e) excess activation of p53.

In a preferred embodiment the process according to the invention is applied to the gene transfer method mentioned above which is described by Curiel et al., 1991; Curiel et al., 1992a; Zatloukal et al., 1992; Cotten et al., 1992; Wagner et al., 1992; Curiel et al., 1992b and in WO 93/07283, in which DNA is introduced into the cell with the aid of conjugates of a ligand for the target cell and a polycation, with the aid of adenovirus, optionally conjugated with a polycation. These publications are expressly included in the disclosure of the present invention. (This method is hereinafter referred to as "adenovirus-aided transferrinfection").

The principle underlying the application of the present invention to this gene transfer system consists in using a transcription- and replication-free adenovirus which is largely reduced in its genetic functions to its endosomolytic properties which are advantageous for increasing gene expression, and further adding the other gene functions of the adenovirus which are necessary or useful for gene transfer, in a controlled manner at a later stage.

However, the process according to the invention may be applied to all the methods for introducing foreign material into the cell, in which the above-mentioned toxicity effects occur, particularly to gene transfer methods, e.g. when recombinant adenovirus vectors are used. Gene transfer methods of this kind are used in vitro and in gene therapy both in vivo and ex vivo, particularly in fibroblasts, haematopoetic cells, endothelial cells or lung epithelial cells.

The use of the process according to the invention may also, in the treatment of eukaryotic cells, include all those applications in which blockage of an apoptotic and/or inflammatory response of the cell is necessary or advantageous. An example of such an expanded application is the transplanting of foreign cells, tissues or organs in which apoptotic reaction of the cells occurs as a result of the immune recognition. By expression of anti-apoptotically effective genes in the cells which are to be transplanted, the apoptosis can be prevented.

In a preferred embodiment of the invention the anti-apoptosis gene is the human Bcl-2 gene (Seto et al., 1988).

In another preferred embodiment the anti-apoptosis gene is the E1B 19K gene of adenovirus type 2 or 5 (White and Cipriani, 1990).

Other examples of anti-apoptosis genes which are suitable for the purposes of the present invention are the BHRF1 gene of the Epstein-Barr virus (Pearson et al., 1987), the baculovirus gene p35 (Sugimoto et al., 1994) and iap (Clem and Miller, 1994), the LMW5-HL gene of African swine fever virus (Neilan et al., 1993) and the ced-9 gene of Caenorhabditis elegans (Sugimoto et al.; 1994).

These gene products act relatively far downstream in the apoptosis signal transmission pathway, i.e. close to the proteases which are directly involved in the degradation processes. Thus, for example, it is assumed that Bcl-2 and Bcl-2-like proteins block the activation of the proteases referred to as ICE or ICE-like. Since these proteases clearly have a crucial function for apoptosis, their blocking is also of critical importance.

Apart from the substances with a Bcl-2-like anti-apoptosis mechanism, consideration must also be given to those which block a component which acts further upstream in the apoptosis signal transmission pathway. Such a component is p53, for example, the activation of which triggers one of the signal transmission pathways which leads to apoptosis. Thus, if the apoptosis triggered by the transfection process proceeds by activating p53, substances which inactivate p53 could be used to block the apoptosis, whilst on the one hand care should be taken to ensure that the blocking is not circumvented by another signal transmission which also leads to apoptosis and on the other hand to ensure that the inactivation of p53 in the cell type in question does not lead to a transformed state.

Examples of genes which inactivate p53 are E1B 55K of adenovirus type 2 or type 5 (White and Cipriani, 1989) or E1-functions of other adenovirus strains, e.g. adenovirus 12 or the CELO virus (Chick Embryo Lethal Orphan Virus), the E6 gene of the human papilloma virus 16 (Levine, 1990), the large T-antigen of SV 40 (McCarthy et al., 1994), and the mdm-2 gene (Momand et al., 1992; Oliner et al., 1993; Chen et al., 1994).

Within the scope of the present invention a screening method has been developed by means of which genes with an anti-apoptotic activity can easily be identified. The method consists in transfecting mammalian cells, e.g. fibroblasts, with a reporter plasmid, e.g. a luciferase plasmid, and monitoring the expression of the reporter gene over a certain length of time. In parallel experiments the cells are additionally transfected under identical conditions with test DNA, e.g. genomic viral DNA fragments or DNA molecules from a cDNA library, in suitable expression vectors. If desired, the cells are additionally transfected, in another test set-up, with a DNA sequence which is known to have the desired anti-apoptotic effect, e.g. with E1B 19K or Bcl-2. In experiments of this kind the anti-apoptotic activity of a test DNA sequence is demonstrated by the fact that, on co-transfection of the cells with this sequence, the expression of the reporter gene is higher than when the cells are transfected with the reporter gene alone. In the case of co-transfection with a gene of a known anti-apoptotic activity, the effect of the test gene can be compared with that of the known gene.

With the aid of this screening method, within the scope of the present invention, first an anti-apoptotically active DNA molecule of the chicken adenovirus type I (CELO=Chicken Embryo Lethal Orphan) was identified.

This DNA molecule is located on an SmaI/HindIII fragment which is located in the CELO virus genome in the region between about 84.3 and about 88.7 mapping units. From the SmaI/HindIII fragment isolated within the scope of the present invention, the nucleotide sequence shown in FIG. 14 was determined (SEQ ID NO:1).

Figure 13:
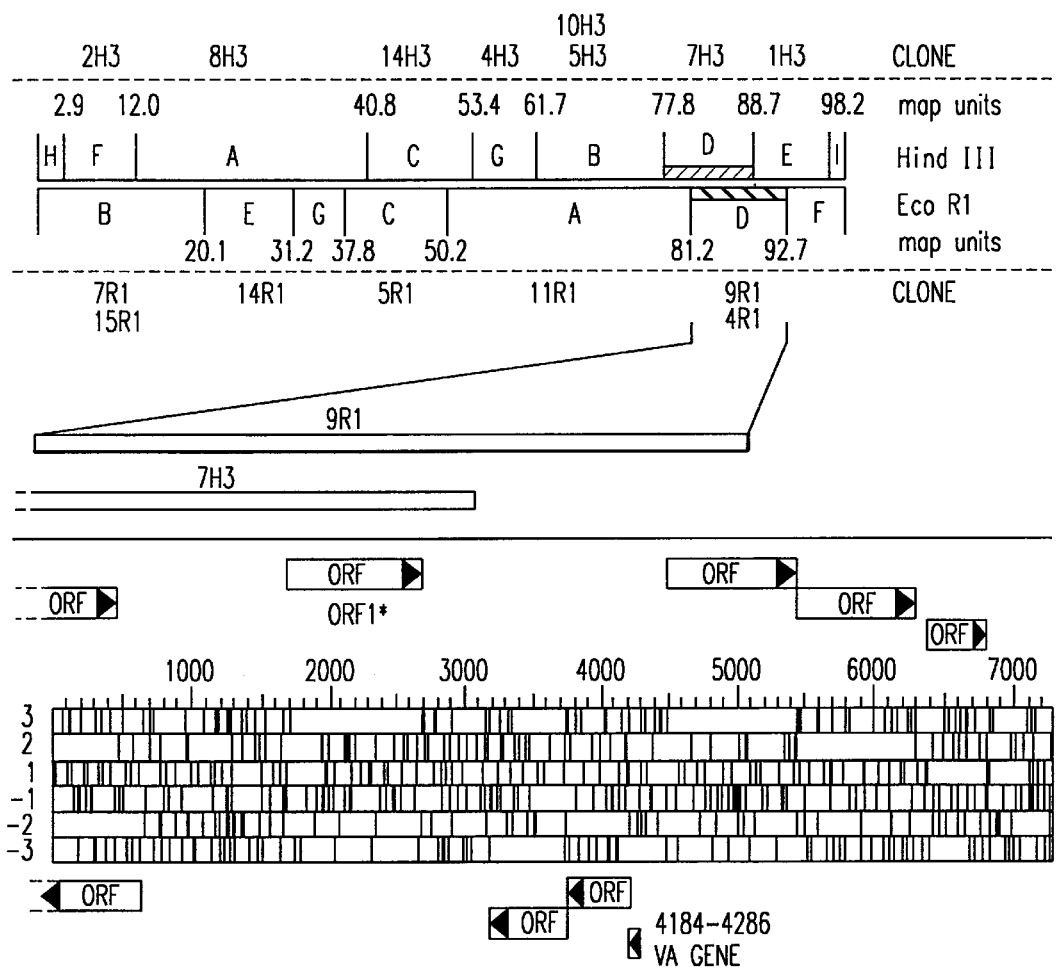

The SmaI/HindIII fragment was obtained from an EcoRI fragment designated 9R1, which is located in the region between 81.2 and 92.7 mapping units (see FIG. 13).

In the process according to the invention, all of the CELO virus fragments obtained which exhibit the anti-apoptotic activity, as for example the SmaI/HindIII fragment as such, may be used.

Alternatively, the EcoRI fragment 9R1, of which the SmaI/HindIII fragment is a partial sequence, may be used as a whole.

Another possibility is to use the HindIII fragment designated 7H3 which is located between mapping units 77.8 and 88.7 on the CELO virus genome. The fragments 9R1 and 7H3 have an overlap area of 80%, the SmaI/HindIII fragment being common to both the fragments and containing the only large open reading frame of this area.

The size of the DNA molecule in the region or environment of the fragment areas specified is not critical.

Preferably, DNA which consists essentially of only the open reading frame is used. This DNA may, if required, also be abbreviated to the section which is responsible for the anti-apoptotic function or mutants may be constructed in order to intensify the activity. Suitable mutants may be selected by testing correspondingly mutated DNA sequences, as described in the Examples, for their ability to intensify gene expression.

In the experiments carried out within the scope of the present invention, the definitive association of an anti-apoptotically acting gene with the open reading frame was carried out by means of controlled in vitro (site specific) mutagenesis; in this way it was possible to establish what is the minimum necessary reading frame for the anti-apoptotic activity, by screening the mutated DNA sections for anti-apoptotic effects. A series of deletion mutants were constructed. It was found that all those constructions by means of which stop codons were inserted into the supposed reading frame and which therefore shortened the resulting proteins in the vicinity of the restriction sites in question eliminated the anti-apoptotic protective effect, whereas the introduction of stop codons outside the open reading frame did not affect this activity.

Analysis of the protein sequence of the presumed open reading frame (the corresponding protein is hereinafter referred to as "GAM-1" and the amino acid sequence is shown in SEQ ID NO:2) also showed a series of seven leucine groups. It is known that this motif folds into a structure (so-called "leucine zipper") which is frequently a site of protein-protein interactions (Busch and Sassone-Corsi, 1990; Lumb and Kim, 1995). It is assumed that the leucine zipper dimerisation domain functions as an alpha-helical structure and consequently the introduction of amino acids such as proline which destroy alpha-helices can impair the zipper dimerisation. It has been found that the introduction of point mutations in the leucine zipper destroys the protective effect of GAM-1 which indicates that the GAM-1 leucine zipper is important for the operation of the protein. Therefore either GAM-1 functions as a homodimer or there are other binding partners for GAM-1.

GAM-1 has no homologies with any of the known anti-apoptotic proteins, including members of the Bcl-2 family, adenovirus 5 E1B 19K, the Bax family, the Baculovirus-IAP family or the nematode protein Ced-3. (Moreover, the complete sequence of the CELO virus genome showed that the CELO virus has no gene which have any homology with the Ad2/5 E1B 19K region. It could be, therefore, that the CELO virus has no E1B 19K region and therefore uses the GAM-1 gene function as a anti-apoptosis gene.)

Thus, according to another aspect, the invention relates to a DNA molecule containing the nucleotide sequence shown in FIG. 14 or SEQ ID NO:1 or a partial sequence thereof coding for a functional gene product having an anti-apoptotic effect.

What is preferred is a DNA molecule with the sequence of the open reading frame shown in FIG. 14 or SEQ ID NO:1, including degenerate variants thereof, or mutants which code for a functional gene product having an anti-apoptotic effect.

According to another aspect the invention relates to the polypeptides derived from the DNA molecules according to the invention, particularly the protein designated GAM-1 (SEQ ID NO:2) which is coded by the open reading frame and functional derivatives thereof.

Although the gene products of E1B 19K, Bcl-2 and GAM-1 have similar protective effects, it may be that they act at different points on the apoptosis pathway. In order to establish this, within the scope of the present invention, various combinations of E1B 19K with GAM-1 or Bcl-2 with GAM-1 were co-transfected with a luciferase reporter gene, and the survival of the cells was determined by luciferase expression compared with cells which were treated only with the genes in question. It was found that the combination of the GAM-1-9R1 fragment with E1B 19K has an improved protective effect compared with the activity of the individual genes, both four days (see FIG. 19, columns 2, 3 and 4) and 22 days (see FIG. 22, traces 3, 4 and 6) after transfection. For Bcl-2 and GAM-1 synergism was observed on day 22.

Signal transmission may occur from the extracellular matrix to the cell. It has been found that the appropriate extracellular environment is crucial to the survival of the cell and that the absence of such an environment can activate a death programme (Meredith et al., 1993; Brooks et al., 1994; survey by Ruoslahti and Reed, 1994). This mechanism could be crucial to determining and obtaining the correct position of the cell within the organism. It has been shown that preventing the adhesion of epithelial cells to the substrate by means of polyHEMA (=poly(2-hydroxy-ethyl-methacrylate; Folkman and Moscona, 1978) leads to apoptosis and that the expression of Bcl-2 can exert a protective effect in this respect. The reduction in gene expression observed after transferrinfection can possibly be put down to a change in the association of the matrix; the mechanism triggered by GAM-1 possibly consists of the prevention of cell death which occurs as a result of the detachment of the cells from the substrate (detachment-induced apoptosis). In order to investigate this question, within the scope of the present invention fibroblasts were transfected on the one hand with a luciferase reporter gene and on the other hand with test plasmids containing various fragments of GAM-1. Two days later, the cells were trypsinised and a defined number of cells were plated out onto polyHEMA-coated cell culture plates. Seven days later the adhering and non-adhering cells were harvested and investigated for luciferase activity. It was found that the protective effect is located within the 7H3- and 9R1-fragments.

In addition, a comparison was carried out between the GAM-1 coded by 9R1 on the one hand and E1B 19K or Bcl-2 on the other hand. In order to do this, cells were transfected either with the luciferase plasmid on its own or with a plasmid which codes for E1B 19K, Bcl-2 or GAM-1. Two days after the transfection a defined number of cells were placed on a series of cell culture plates with a poly-HEMA coating of graduated concentration and after seven days the surviving cell population was determined by measuring the luciferase expression which remained. By comparing with control cells which expressed only the luciferase gene, a 20-fold reduction in luciferase expression was found when the cells were placed on plates with increasing poly-HEMA concentrations. It was observed that the surfaces coated with the highest polyHEMA concentrations caused total wipeout of the cell population. Bcl-2 would appear to have a more powerful effect than E1B 19 K or GAM-1; the luciferase expression obtained without polyHEMA remained unchanged with Bcl-1 even at the highest poly-HEMA concentration.

Within the scope of the present invention it was established that E1B 19K, Bcl-2 and GAM-1 have a protective effect against apoptosis triggered by the detachment of the cells from a substrate.

The DNA molecules coding for GAM-1 which have been identified within the scope of the present invention may also be mutated, provided that either the mutations do not change the amino acid sequence or that the changes do not affect any amino acids which are essential to the function.

In the preferred application of the inventive process to adenovirus-aided transferrinfection, the anti-apoptosis gene is easily incorporated in the transfection complexes in the form of a plasmid together with the plasmid which contains the DNA sequence and the expression of which in the cell is intended to achieve the desired effect (hereinafter referred to as "effective DNA"), e.g. a therapeutically active gene. It is then complexed together with the plasmid which carries the effective DNA, e.g. with transferrin-polylysine and adenovirus-polylysine. The molar ratio of effective gene and anti-apoptosis gene can be determined by titration, by measuring the expression of the effective gene with various proportions of anti-apoptosis gene under otherwise identical conditions over a long period. For the purposes of the present invention a ratio of 5:1 was selected which proved favourable. Since the gene products of some anti-apoptosis genes exhibit very powerful effects, smaller amounts might also be used. An upper limit set by general toxicity may also be obtained by titration.

It is also possible to integrate the therapeutically effective DNA sequence and the anti-apoptosis gene together in a single plasmid; in this case the molar ratio of the two genes is 1:1 when they are present in one copy each on the plasmid.

Within the scope of the present invention it was found that cell death is triggered by the entry of adenovirus, even in the absence of viral gene expression. The simultaneous introduction of an active adenovirus-E1-region provided relief from the apoptosis; experiments with plasmids which carried individual E1 genes identified E1B 19K as the gene responsible for the protective effect. Moreover, in the apoptosis phenotype, it was demonstrated that the simultaneous introduction of the Bcl-2 gene can also block the toxicity.

In order to investigate the activation of the inflammatory response to the entry of adenovirus, for the purpose of the present invention, two cell lines were established which contain the luciferase gene under the control of promoters which respond to two of the most important transcription factors activated during inflammation, namely NF-IL-6 and NF-κB. This provided the precondition of rapidly investigating the activation of these transcription factors as a response to the entry of adenovirus or the transfection complex. In order to test the activation of NF-κB, a construct was used which contains the luciferase gene under the control of a simple TATA box and three NF-κB binding elements. Furthermore, the luciferase construct responding to NF-IL-6/NF-κB and driven by the IL-6 promoter was used. The activation behaviour of the two reporter cell lines confirmed that the promoters respond not only to their activators LPS and PMA as characterised earlier but also to adenovirus, both to non-inactivated and to psoralen/UV-inactivated adenovirus (Table 1). It was found that activation by psoralen-inactivated virus occurred to the same extent as with non-inactivated virus. This supports the theory that it is not the early virus gene expression which activates these factors but rather the binding and the entry of adenovirus.

The procedure of external treatment with anti-inflammatory substances defined in step b) under i) may consist, for example, of treatment with retinoic acid or other retinoids, which have been reported to inhibit the IL-1-induced production of IL-6 by lung fibroblasts (Gross et al., 1993; Zitnik et al., 1994). The mode of activity of this type of substance would appear to consist in controlling the concentration of the IL-6-mRNA.

Another type of substance for inhibiting the inflammatory host response consists of the glucocorticoids, which have been shown to inhibit the production of IL-6 and/or IL-8 as a response to inflammatory stimuli (Ray et al., 1990; Barber et al., 1993; Wertheim et al., 1993).

Within the scope of the present invention it has been demonstrated that the glucocorticoid dexamethasone intensifies gene expression both on its own and in conjunction with the anti-apoptosis gene E1B 19K.

Dexamethasone acts on the activation of the enzyme phospholipase A2, which occurs as one of the consequences of inflammation (Barnes and Adcock, 1993). This enzyme is activated as a reaction to numerous inflammatory signals and leads to the release of arachidonic acid.

Another group of anti-inflammatory substances which may be used within the scope of the present invention are inhibitors of arachidonic acid metabolism.

Arachidonic acid is metabolised by the cyclooxygenase pathway into pro-inflammatory prostaglandins and thromboxanes. This pathway, which is diagrammatically shown in FIG. 12 can be inhibited by the cyclooxygenase inhibitors Aspirin (acetylsalicylic acid), Ibuprofen or Indomethacin (Flower et al., 1985). Further activation by arachidonic acid involves 5-lipoxygenase processing, as a result of which leukotrienes are formed. 5-Lipoxygenase can be inhibited by NDGA (Nordihydro-guaiaretic acid; Burkart and Kolb, 1993; Cifone et al., 1993; Conti et al., 1993; Pasquale et al., 1993; Rao et al., 1993) or by 5,8,11-eicosatriynoic acid (Pace et al., 1993). Other inhibitors of 5-lipoxygenase have been described by McMillan and Walker, 1992.

Apart from being treated with the above-mentioned anti-inflammatory substances, the cells may also be treated with anti-inflammatory polypeptides, such as IL-10 or TGF-β.

For the external treatment of the cells the anti-inflammatory substance is appropriately added to the medium.

According to step b) ii) the anti-inflammatory substance is introduced into the cell as it is or, according to a preferred embodiment, in the form of the DNA which codes for it, e.g. in the form of a plasmid which contains a sequence coding for an anti-inflammatory protein such as IL-10 (Moore et al., 1990) or TGF-β (Massague et al., 1987).

An anti-inflammatory substance which is preferably used within the scope of the present invention is VA1. Adenovirus VA1-RNA is a small RNA molecule synthesised by RNA polymerase III, which is responsible for the efficient expression of the virus genome.

In the light of reports that double stranded RNA activates NF-κB (Visvanathan and Goodbourn, 1989) and in the light of the known activity of VA1-RNA in blocking the activation of dsRNA-activated kinase p68, investigations were carried out to see whether the introduction of a VA1 gene blocks the activation of NF-κB, which is triggered by the entry of transfection complexes of adenovirus/polylysine/DNA.

It has been established, within the scope of the present invention, that the expression of the adenovirus VA1 gene (brought about by incorporating the DNA which codes for VA1 into the transfection complex) reduced the activation of NF-κB by adenovirus to 1.5 times the base value. Thus, the expression of the adenovirus VA1 gene can be used during transfection to modulate the activation of NF-κB which is triggered by the transfection process.

The observation made within the scope of the present invention to the effect that the VA1 expression inhibits the activation of inflammatory cytokines would appear to be due to a phenomenon which is independent of the increase in the stability of the mRNA or the quantity thereof, as reported for the calcium phosphate method. The inhibition of the p68-kinase activation might possibly be crucially involved in this phenomenon.

The VA1 can be imported into the cell as an RNA molecule or, in a preferred embodiment, in the form of VA1-DNA. A plasmid which contains the VA1 sequence, optionally in multiple copies, may be integrated in transfection complexes together with the plasmid with the effective DNA and the plasmid with the anti-apoptosis gene. It is also possible to combine two of the three sequences, or even all three, on a single plasmid.

One example of a triple combination which could be used in the course of gene therapy would be a combination of a DNA containing the factor VIII sequence as therapeutically effective DNA, an anti-apoptosis gene such as bcl-2 or E1B 19K and VA1-DNA.

As an alternative to VA1-DNA, genes may be used which have an activity corresponding to VA1, e.g. EBER of the Epstein Barr Virus (Clarke et al., 1990; Clarke et al., 1991) or the TAR-RNA of the HIV virus (Gunnery et al., 1990).

According to another aspect the invention relates to a transfection complex containing a nucleic acid molecule to be expressed in the cell which is complexed with a polycation optionally conjugated with a ligand for the target cell, as well as adenovirus or an adenovirus-polycation conjugate, the complex further containing a DNA molecule with anti-apoptosis effect and/or a DNA molecule coding for a substance having an anti-inflammatory effect.

The invention also relates to a pharmaceutical preparation containing a transfection complex of this kind in which the nucleic acid molecule to be expressed in the cell is a therapeutically or gene-therapeutically active DNA molecule. Apart from the transfection complex, the pharmaceutical preparation contains the usual additives for use on cells, such as nutrients, etc.

LIST OF FIGURES

Figure 1B:
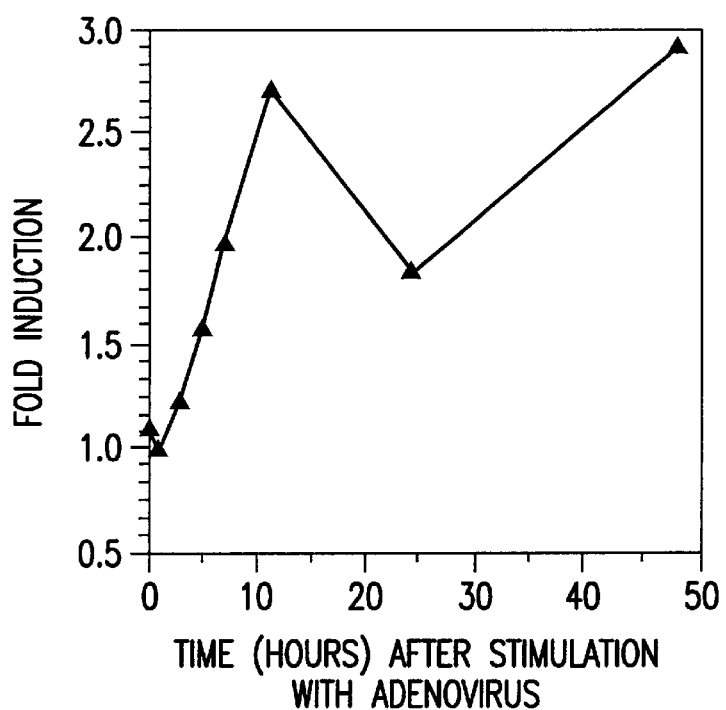

FIG. 1: Time sequence of the activation of NF-IL-6 and NF-κB.

Figure 2:
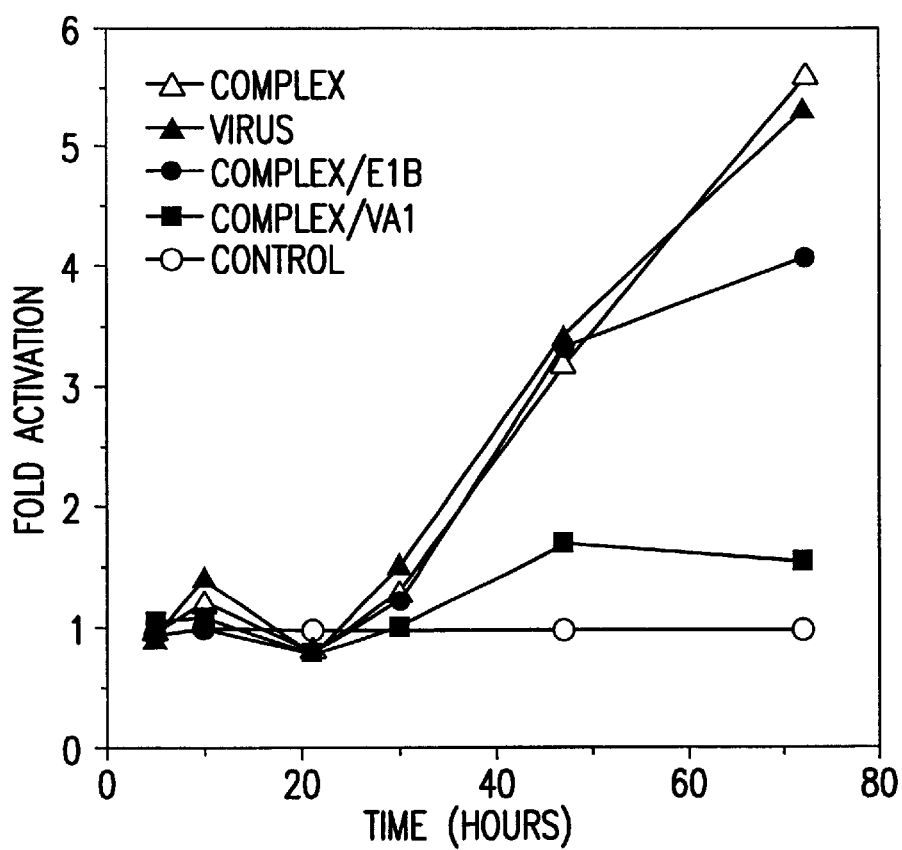

FIG. 2: Blocking of the activation of NF-κB by the expression of VA1.

Figure 3:
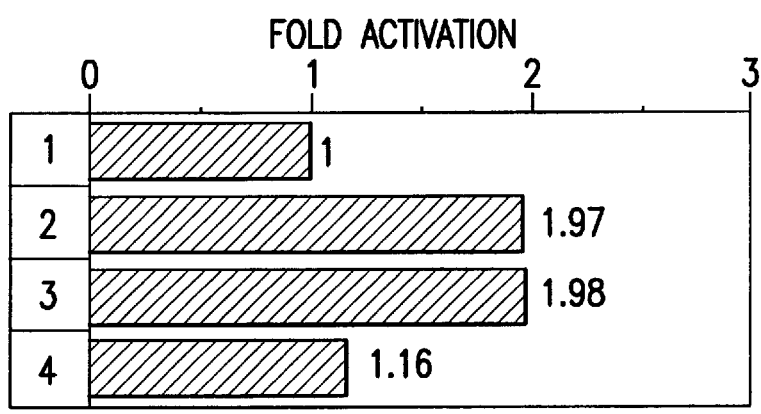

FIG. 3: Blocking of the activation of the IL-6 promoter by the expression of VA1.

Figure 4:
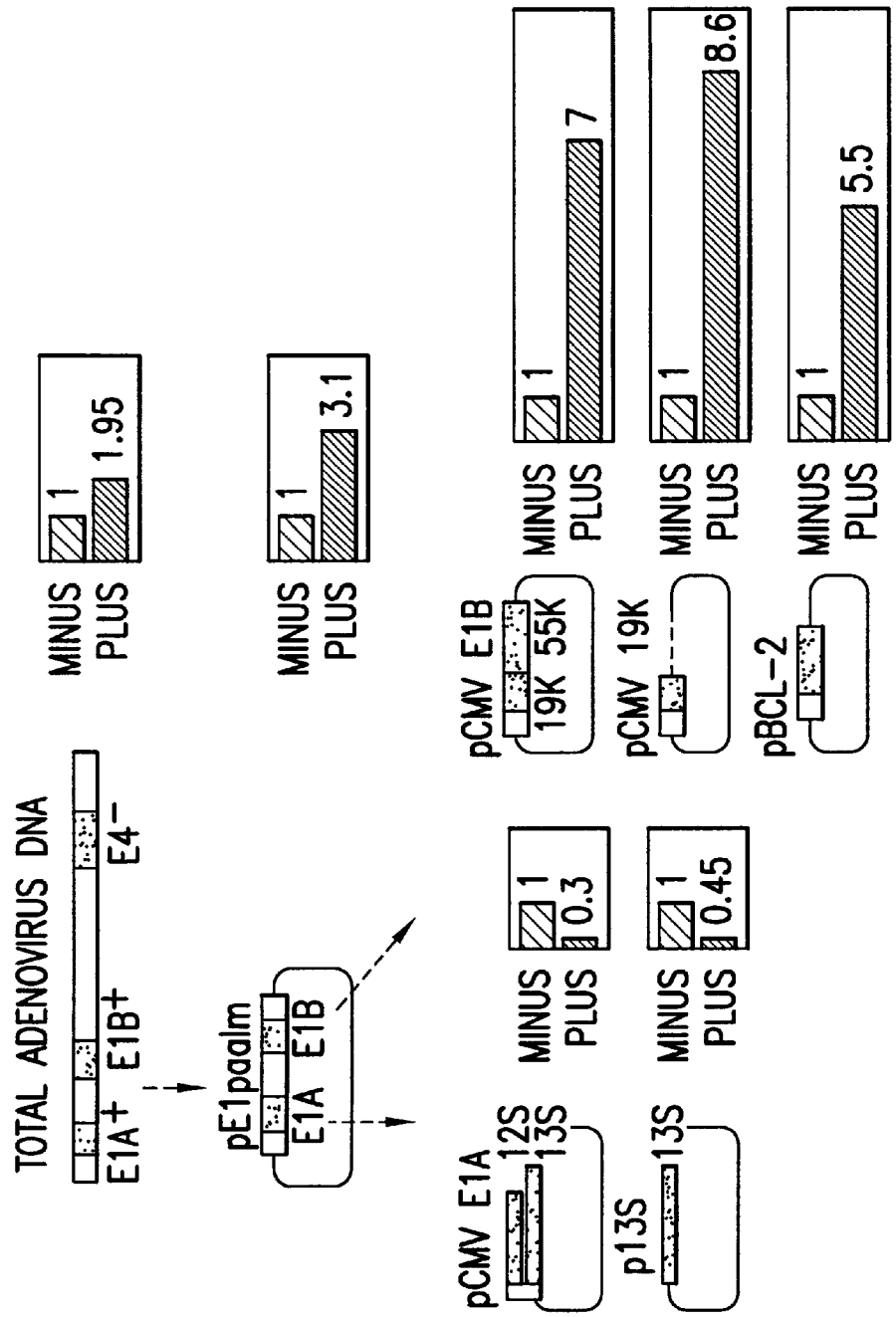

FIG. 4: Influence of the expression of E1A, E1A 13S, E1B, E1B 19K and Bcl-2 on gene expression.

Figure 5A:
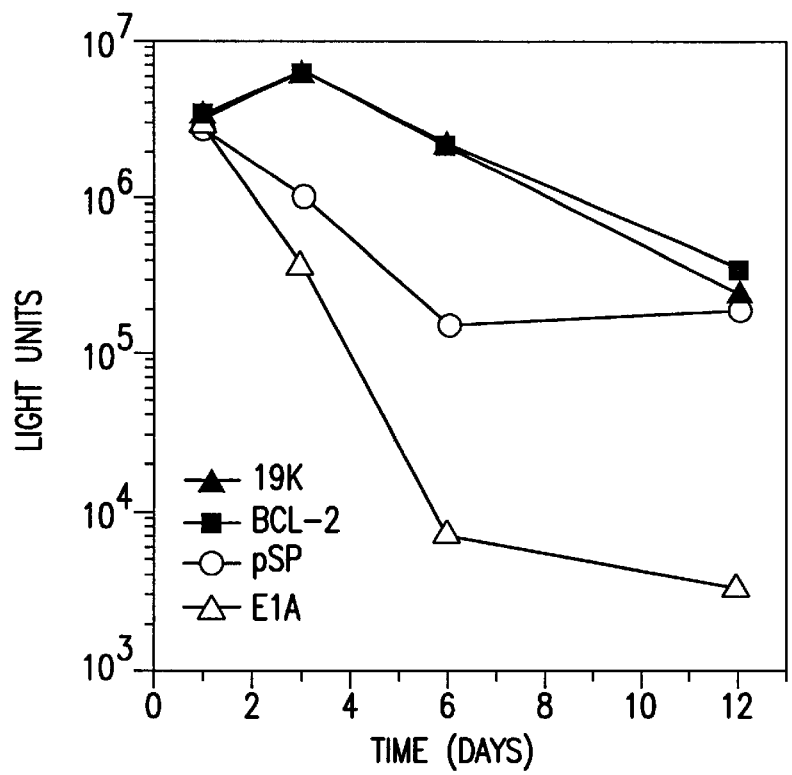
Figure 5B:
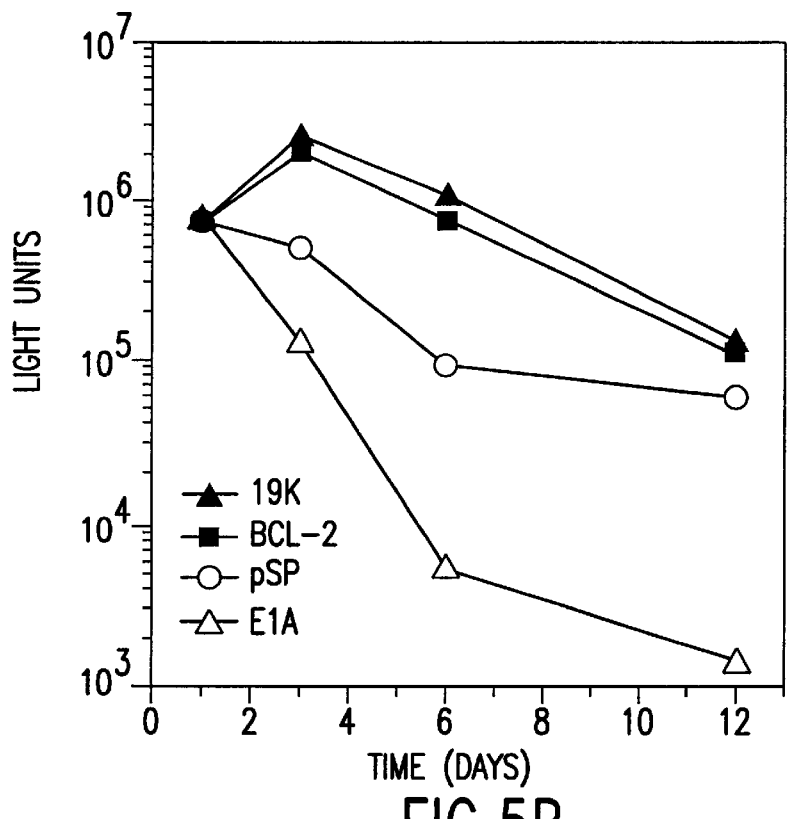
Figure 5C:
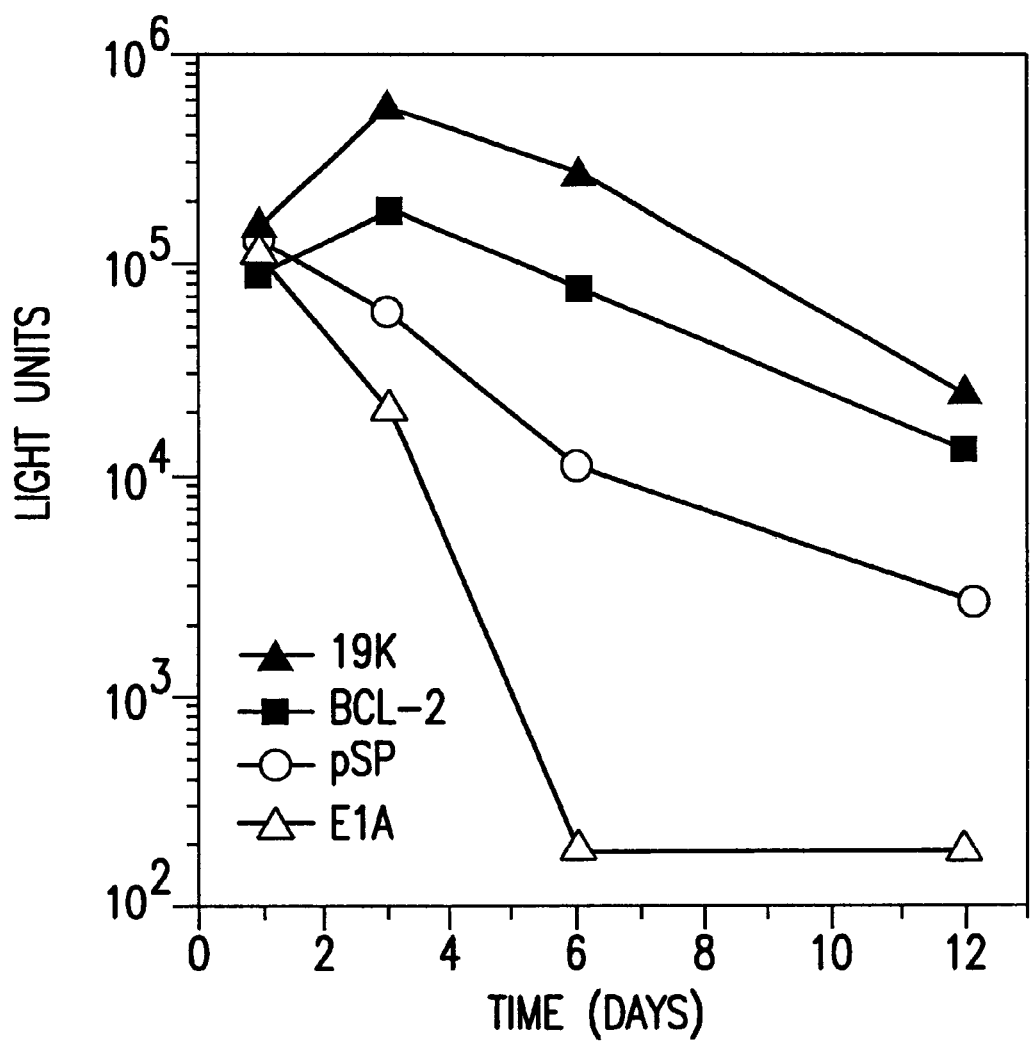

FIGS. 5A–C show the influence of the expression of E1B 19K, E1A and Bcl-2 on gene expression with different virus dosages.

Figure 6:
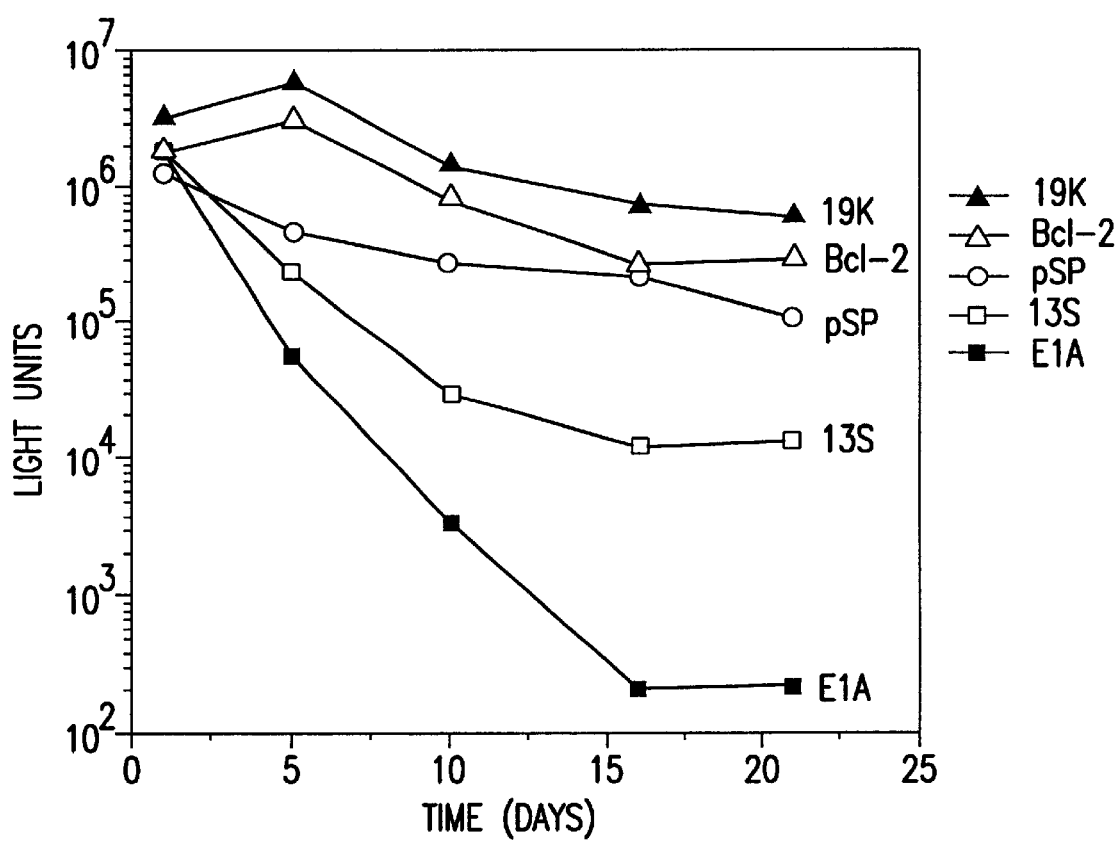

FIG. 6: Influence of the expression of Bcl-2, E1B 19K, E1A and E1A 13S on long-term gene expression.

FIG. 7: Influence of transfection on the morphology of fibroblasts.

Figure 8:
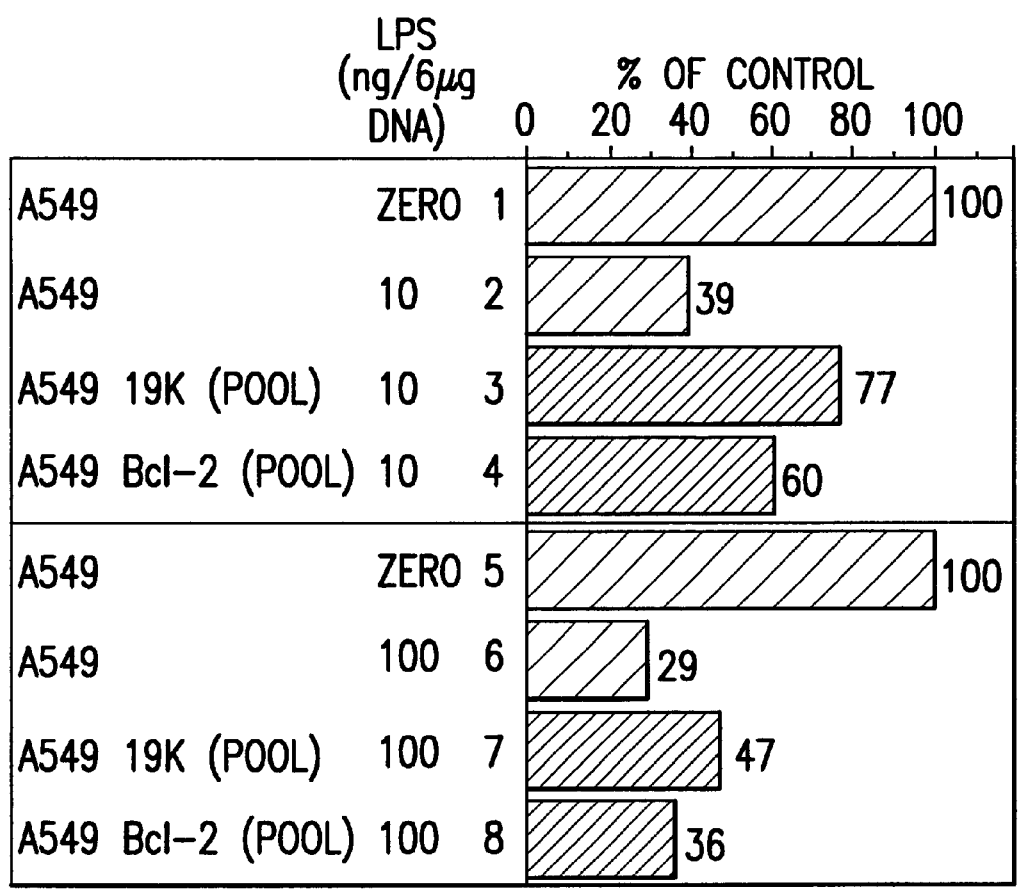

FIG. 8: Inhibition of the toxicity caused by adenovirus or LPS, by pre-expression of E1B 19K and Bcl-2.

Figure 9:
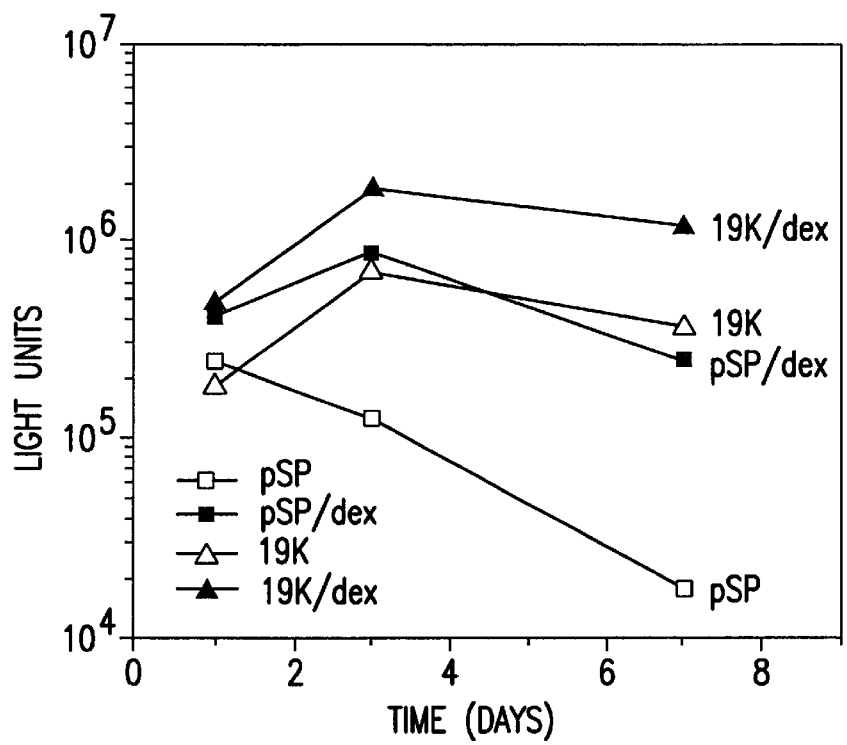

FIG. 9: Increase in gene transfer by dexamethasone alone or in conjunction with E1B 19K.

Figure 10:
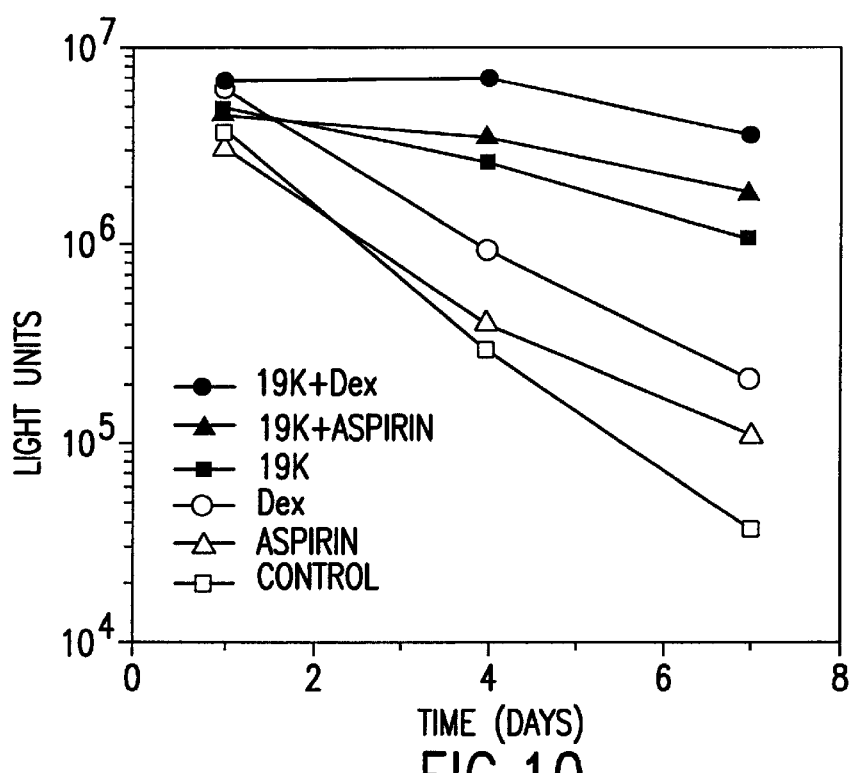

FIG. 10: Increase in gene transfer by dexamethasone or Aspirin alone or in conjunction with E1B 19K.

Figure 11:
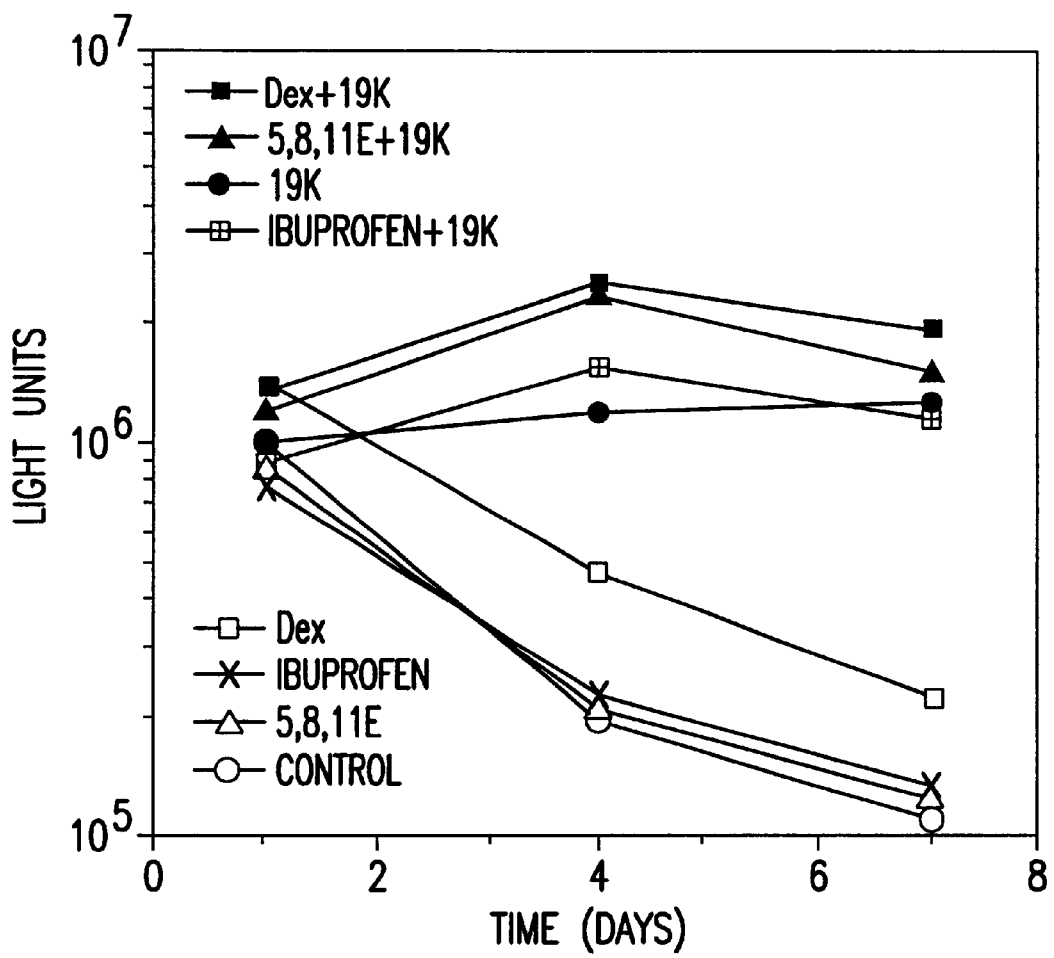

FIG. 11: Effect of dexamethasone, Ibuprofen or 5,8,11-eicosatriynoic acid on its own or in the presence of E1B 19K.

Figure 12:
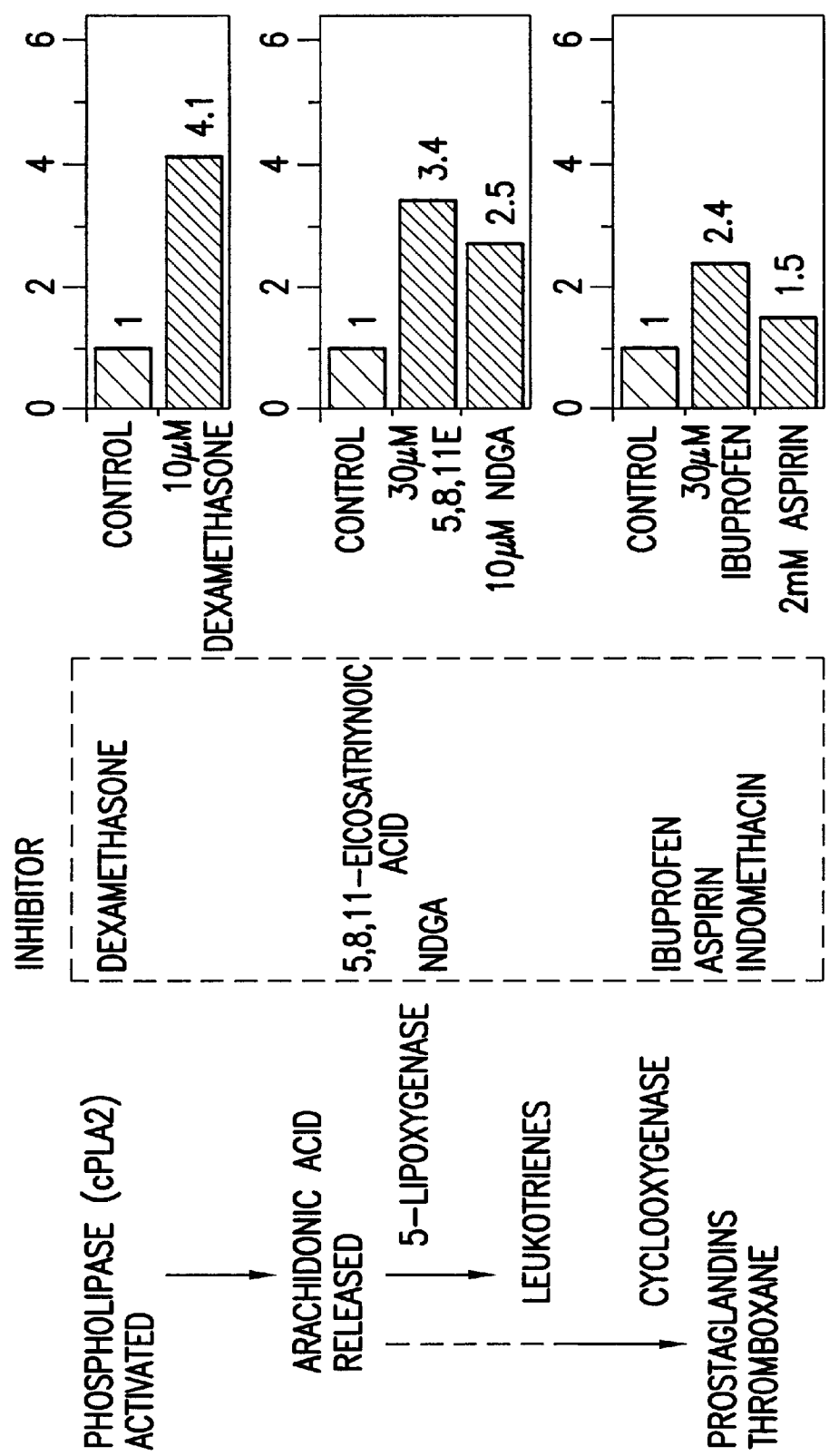

FIG. 12: Comparison of the increase in gene expression by means of various inhibitors of arachidonic acid metabolites.

FIG. 13: Restriction map of the CELO virus genome and map of the open reading frame of EcoRI fragment 9R1.

FIG. 14: Sequence of the CELO virus SmaI/HindIII fragment of 9R1 (9R1S/H3).

Figure 15:
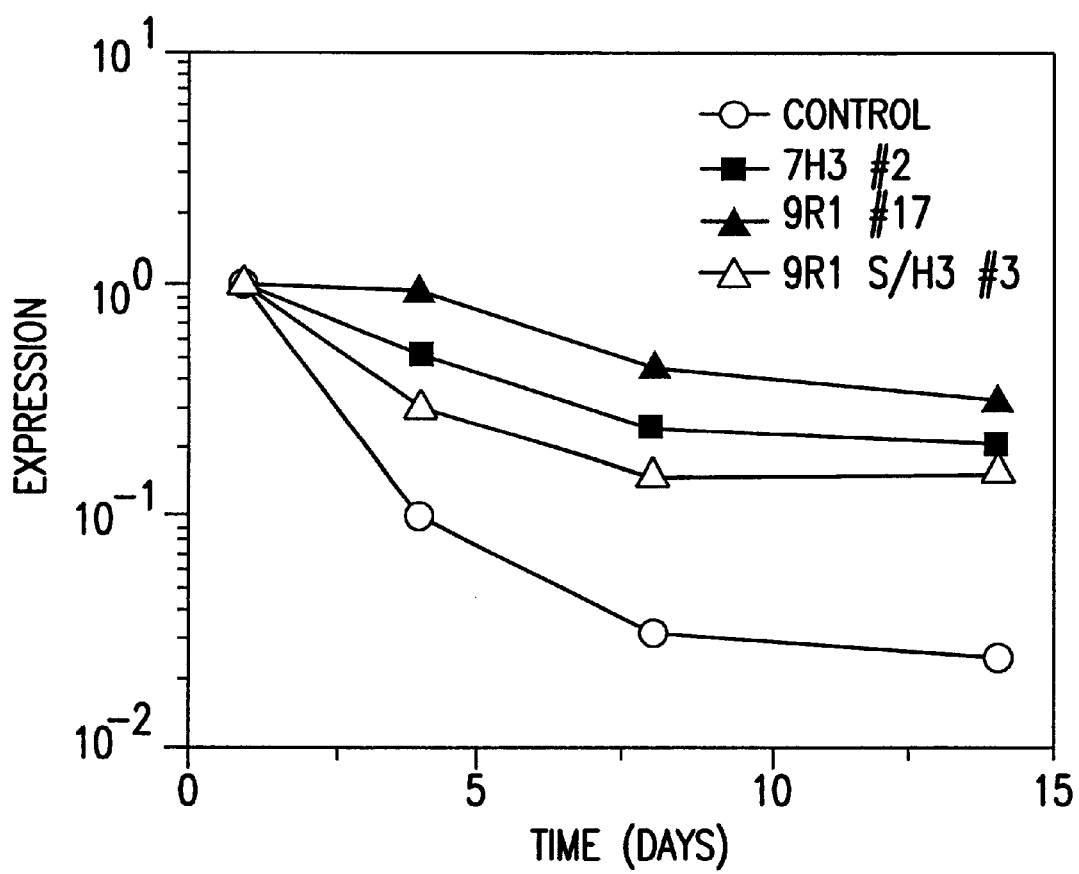

FIG. 15: Gene expression in the presence of the fragments 7H3, 9R1 and 9R1S/H3.

Figure 16:
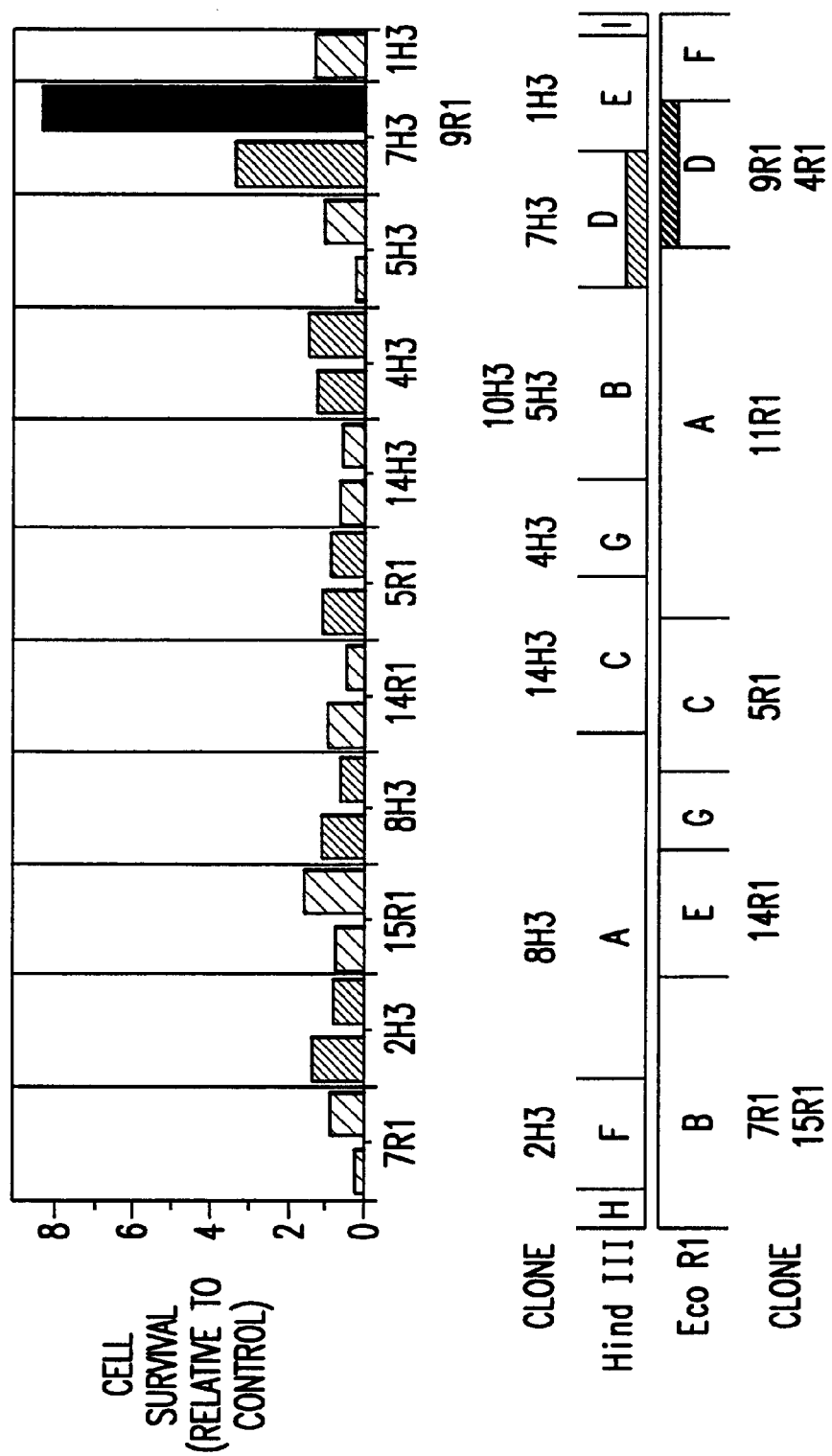

FIG. 16: Anti-apoptotic effect of various CELO virus fragments.

Figure 17:
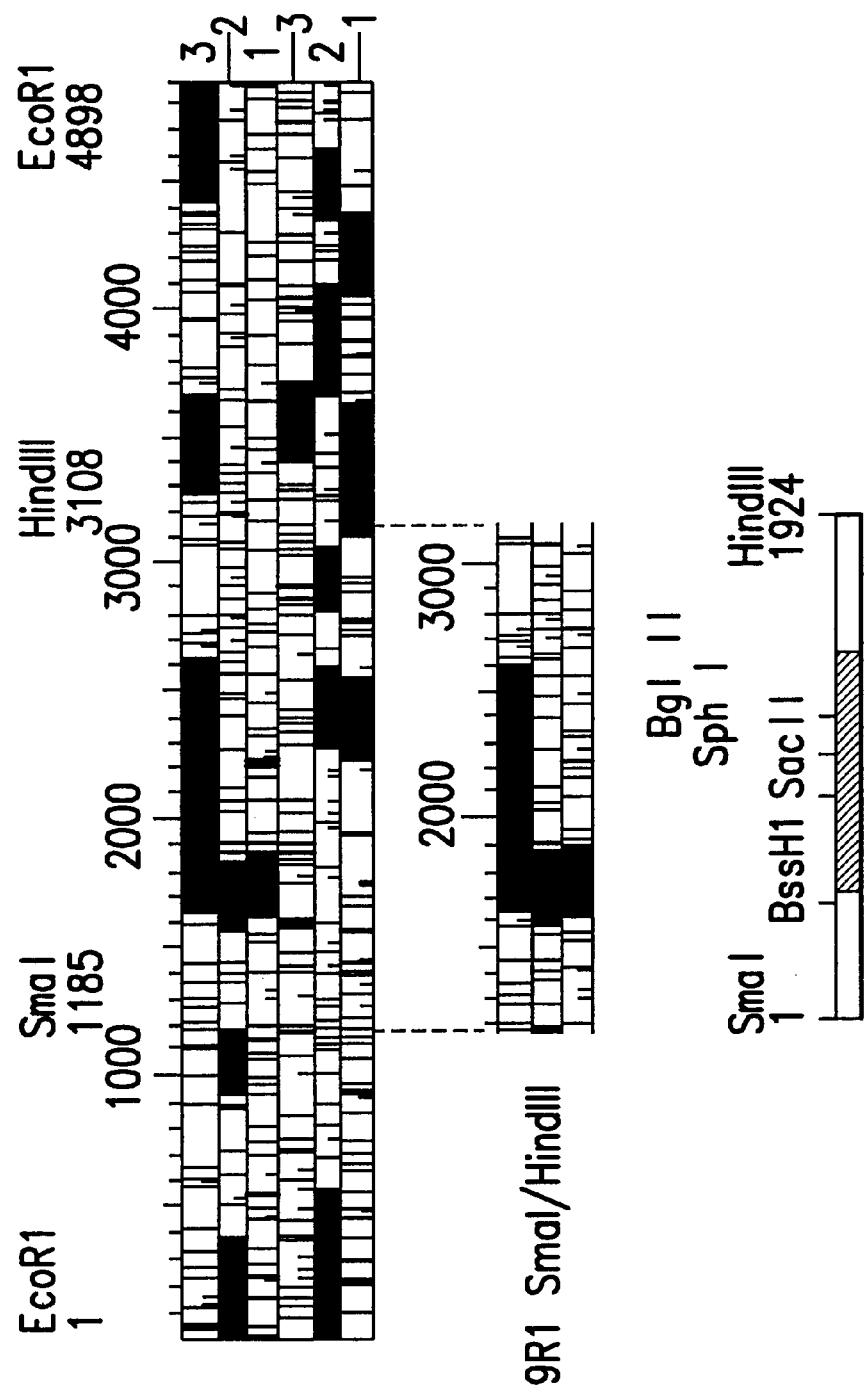

FIG. 17: Open reading frame of the EcoRI fragment of CELO virus.

Figure 18:
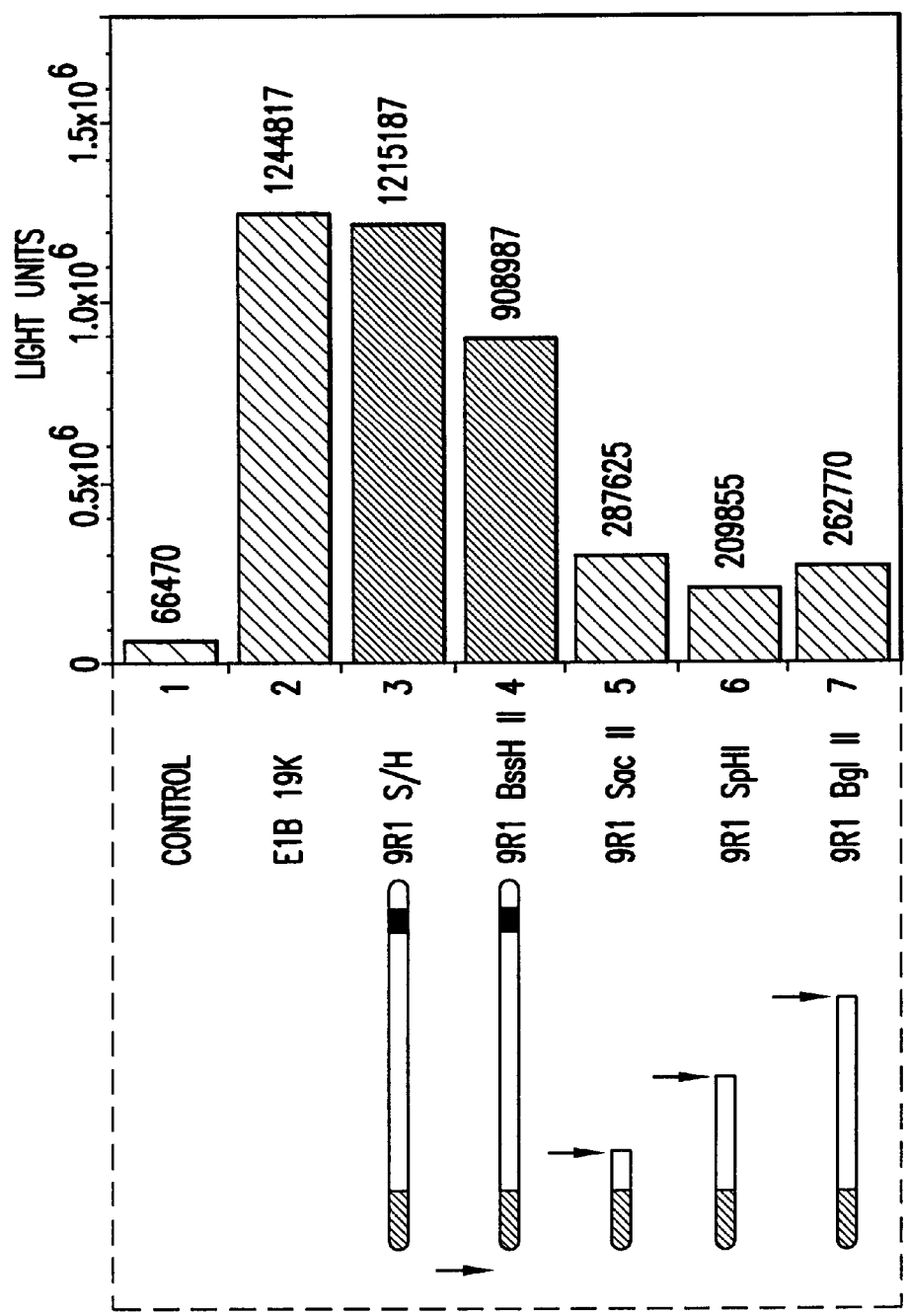

FIG. 18: Association of the anti-apoptotic activity with the correct reading frame. Comparison of different mutants.

Figure 19:
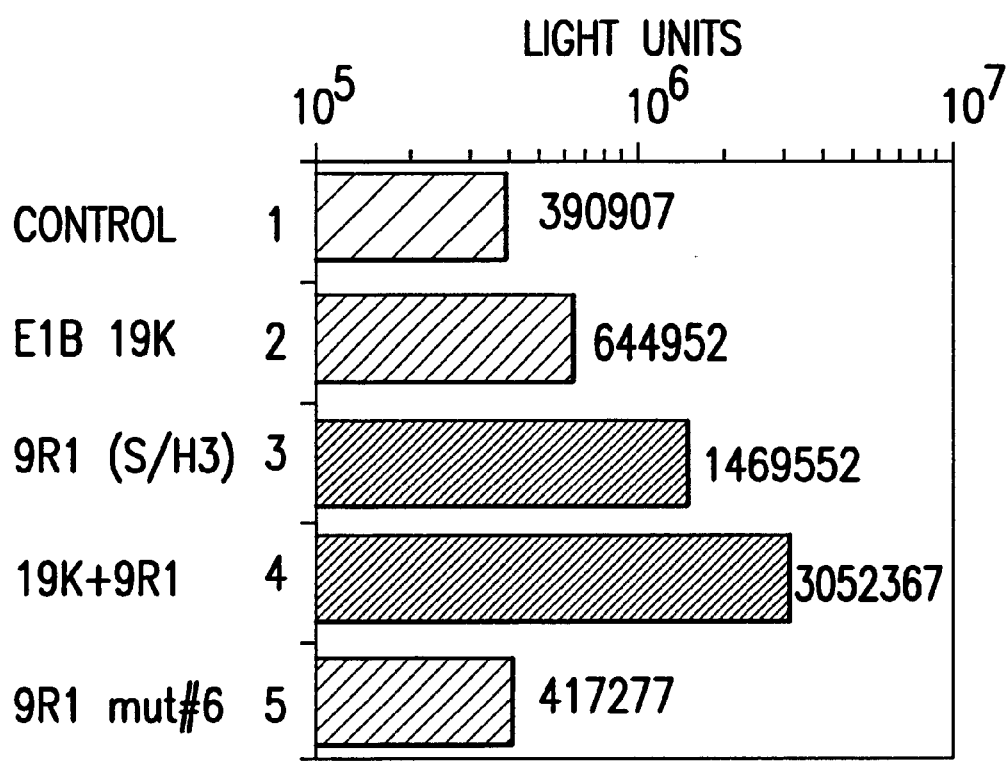

FIG. 19: Influence of the mutation of the leucine zipper on the anti-apoptotic effect.

Figure 20:
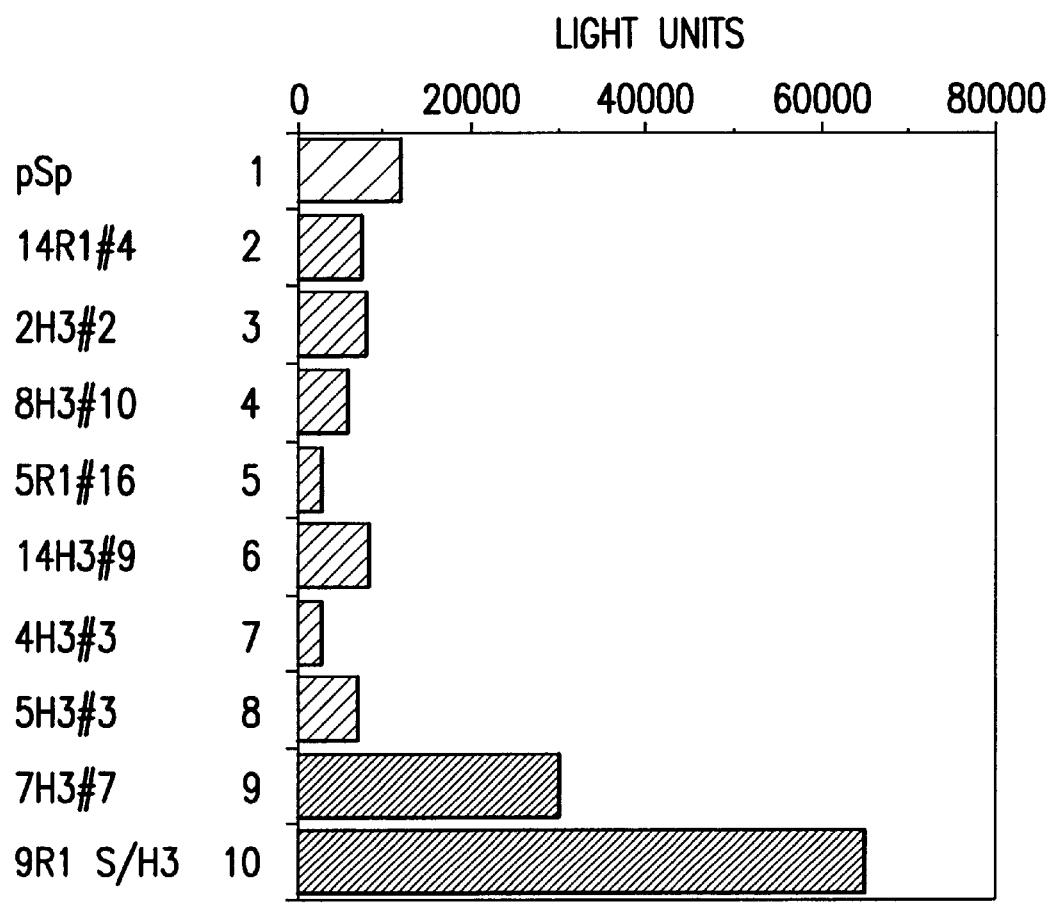

FIG. 20: Effect of the CELO virus gene on the apoptosis triggered by detachment of the cells from the substrate.

Figure 21:
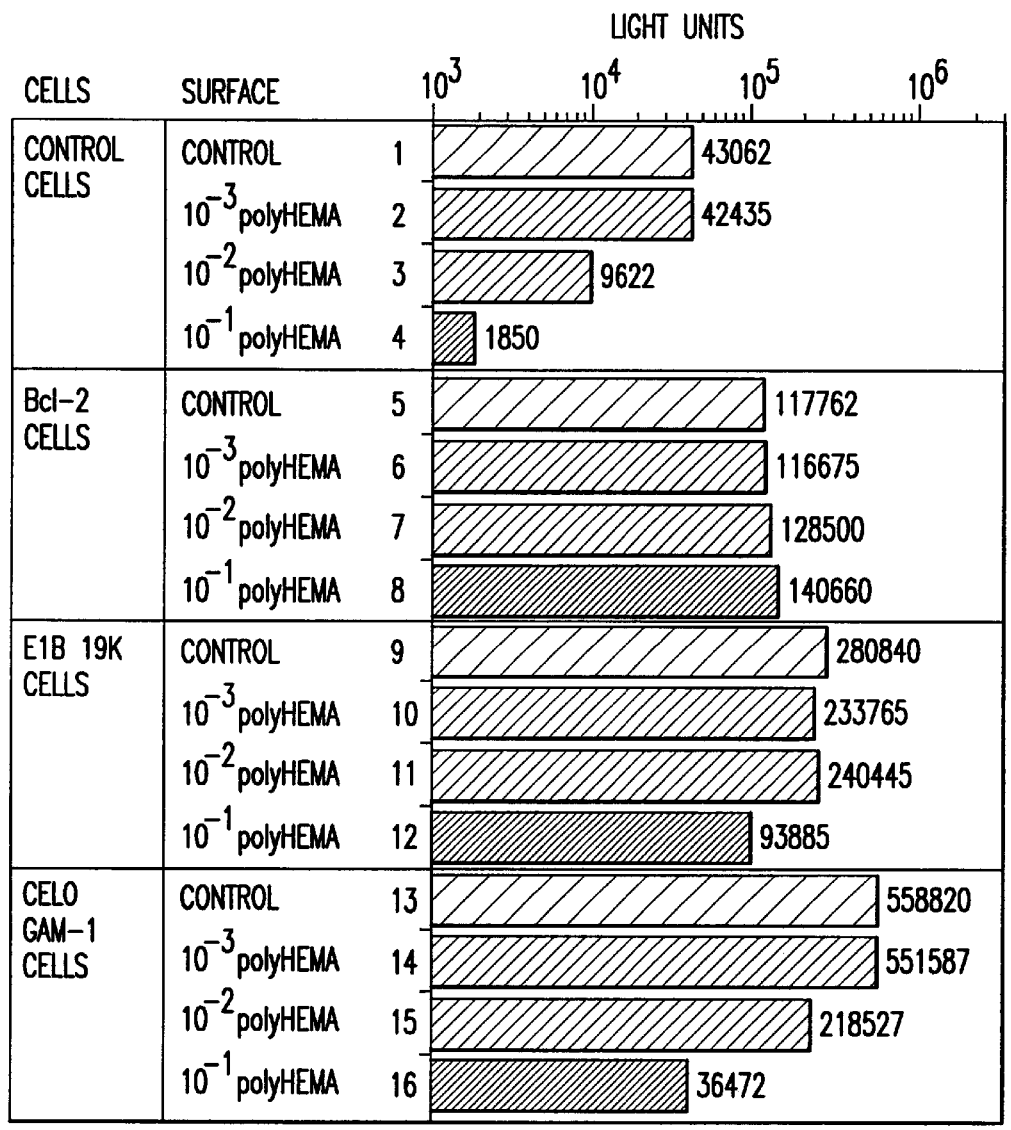

FIG. 21: Comparison of the activity of various anti-apoptotically acting genes on the apoptosis triggered by detachment of the cells from the substrate.

Figure 22:
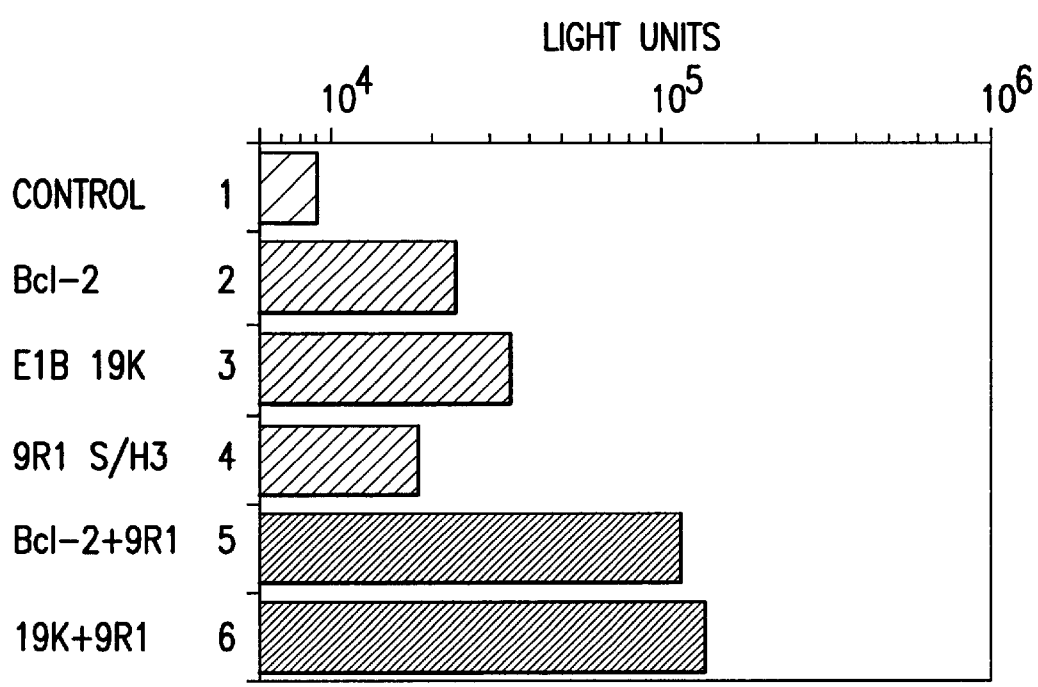

FIG. 22: Effect of the combinations of various genes having an anti-apoptotic effect.

In the following Examples, unless otherwise stated, the following materials and methods were used:

a) DNA Plasmids i) Expression Plasmid for the Adenovirus-VA1 Sequence

First of all the entire E1 region of adenovirus type 5 (nucleotide 1-5778) was obtained by digesting the adenovirus dl1014-DNA (Bridge and Ketner, 1989) with XhoI plus AseI. This fragment was treated with Klenow polymerase and ligated into the SmaI site of the plasmid pAALM (obtained from pSP64 (Boehringer Mannheim), by replacing the small EcoRI/PvuII fragment (bp 53-bp 232) with the EcoRI/PvuII fragment (bp 59-bp 104) of pSPT18 (Boehringer Mannheim)), thereby obtaining pE1paalm. The VA1 expression plasmid pXVAH was constructed by inserting the 5324 bp HindIII fragment (nucleotide 6241-11656) of the adenovirus DNA into the HindIII site of pAALM in order to obtain pHVAH. pHVAH was then cleaved with XbaI and religated in order to obtain pXVAH (in this way a large fragment was removed, from the XbaI site in pAALM to the XbaI site at position 10589 of the adenovirus sequence). The clone pXVAH obtained contained the adenovirus sequence of nucleotide 10589-11565.

ii) Luciferase Reporter Plasmid pNF-κB-Luc

The plasmid pNF-κB-Luc responding to NF-κB was constructed as a derivative of the plasmid pTK3kbB described by Boehmelt et al., 1992. In order to do this, pTK3kbB was cut with XhoI and NcoI in order to remove the majority of the sequence coding for CAT, treated with Klenow enzyme and ligated with a Klenow-treated HindIII/SspI fragment of pRSVL, containing the luciferase sequence (De Wet et al., 1987). This yielded the plasmid p3K-Luc which contains a triple binding site for the transcription factor NF-κB plus the luciferase sequence, driven by a thymidine kinase (TK) TATA box.

iii) Luciferase Construct pIL-6-Luc

The construct described by Matsusaka et al., 1993 was used, which contains the luciferase sequence driven by the IL-6 promoter.

iv) Expression Plasmid for E1A 13S

The expression plasmid designated p13S, described by Kédinger et al., 1984, was used, which makes use of the endogenous E1A promoter in order to drive the E1A 13S-cDNA.

v) Expression Plasmids for E1A, E1B and E1B 19K

The expression plasmids used, designated pCMVE1A, pCMVE1B and pCMV19K were described by White and Cipriani, 1989 and 1990.

vi) Expression Plasmid for Bcl-2

The expression plasmid designated pCMV-Bcl-2 was prepared by cloning the human Bcl-2 cDNA, flanked by two EcoRI sites (Seto et al., 1988), downstream from a CMV-Immediate-early-Promoter into the expression plasmid pBK-CMV (Stratagene).

vii) Plasmid DNA pCMVL

The construction of the plasmid is described in WO 93/07283.

viii) Plasmid DNA pCMVβgal

The plasmid described by Lim and Chae, 1989, was used.

b) Adenovirus dl1014 DNA Preparation

The E4-deficient adenovirus 5, dl1014 (Bridge and Ketner, 1989) was cultivated in the complementary cell line W162 (Weinberg and Ketner, 1983). Pellets of infected cells were suspended in amounts of 2 ml/2×10$^7$ cells in 20 mM HEPES, pH 7.4, 1 mM PMSF (phenylmethylsulphonylfluoride) and subjected to three freeze-thaw cycles (liquid nitrogen, 37° C.). The suspension was then mixed with an equal volume of freon in a vortex and centrifuged for 10 minutes at 3,000 rpm (Heraeus Sepatech, 2705 Rotor). The aqueous (upper) phase was taken off and the freon phase was treated with ⅕ of a volume of 20 mM HEPES, pH 7.4, in a vortex and centrifuged again. The aqueous phases were combined, transferred into a Beckman VTi50 centrifuge tube (15 ml/tube) and layered with 15 ml of 1.2 g/cm$^3$ CsCl/20 mM HEPES, pH 7.4 and 7 ml 1.45 g/cm$^3$ CsCl, 20 mM HEPES pH 7.4. The samples were centrifuged for 40 minutes at 20° C. in a Beckman VTi50 rotor at 49,000 rpm. The lower opalescent band of mature virus particles at 1.34 to 1.35 g/cm$^3$ (measured by refractive index) and the upper band (immature particles at 1.31 to 1.32 g/cm$^3$) were collected separately and subjected to equilibrated centrifuging (for more than 4 hours) at 63,000 rpm in a VTi65 rotor. The opalescent virus bands (either 1.31 g/cm$^3$ immature or 1.34 g/cm$^3$ mature) were harvested. Biotinylation of the virus particles obtained with N-hydroxysuccinimide-biotin (Pierce), inactivation with 8-methoxypsoralen/UVA and purification by gel filtration using a Pharmacia PD10 column, equilibrated with HBS/40% glycerol, were carried out as described in WO 93/07283 or by Wagner et al., 1992 and Cotten et al., 1992. The virus samples were quantitatively analysed by means of the protein concentration (Biorad Bradford Assay with BSA as standard), using the equation 1 mg/ml of protein=3.4× 10$^{12}$ adenovirus particles/ml (Lemay et al., 1980).

c) Transferrin-Polylysine-Conjugates (TfpL)

In order to synthesise conjugates of transferrin and polylysine with a chain length of 290 lysine groups, the method described by Wagner et al., 1991, was used.

d) Streptavidine-Polylysine-Conjugates (StpL)

The conjugates were prepared as described in WO 93/07283, using polylysine 250.

e) Adenovirus/DNA Complexes

Samples of biotinylated, psoralen/UV-inactivated adenovirus dl1014 (8 μl, 1×10$^{12}$ particles/ml) were diluted in 150 μl of HBS and mixed with 1 μg of StpL in 150 μg of HBS for 30 minutes at ambient temperature. Aliquots of 6 μg of plasmid DNA (in the case of mixtures of pCMVL-DNA and another plasmid the ratio was 5:1) were diluted in 100 μl of HBS and then mixed with the adenovirus/StpL solution for 30 minutes at ambient temperature. Finally, a 100 μl aliquot of HBS, containing 5 μg of TfpL, was added to each sample, followed by 30 minutes' incubation at ambient temperature.

Aliquots of these transfection complexes were then added to the cells as described individually in the Examples (generally 10 to 30 µl/20,000 cells).

f) Reporter Cell Lines

In order to prepare the clonal cell lines, containing the reporter plasmid pNF-κB-Luc or pIL-6-Luc, the human lung cancer cell line A549 (ATCC CCL 185) was used as starting material. The plasmids were co-transfected with the neomycin-phosphotransferase-expression plasmid designated pMuatt (a pUC19 plasmid containing the TKneo-sequence; Grosveld et al., 1982) using the transfectam method (Behr et al., 1989) and selected for cells which are resistant to 400 µg/ml of G418 (Sigma). Clonal derivatives which expressed luciferase after induction by PMA were identified and expanded.

In a similar manner, A549 cells were obtained which contain the expression plasmid for Bcl-2 or E1B 19K, except that the neomycinphosphortransferase plasmid pSVneo (Clontech) was used instead of pMuatt and pools of G418 resistant clones were used instead of pure populations.

g) Human Fibroblasts

After surgical removal, skin biopsies were added to 4° C. DMEM containing 10% heat-inactivated FCS, 2 mM glutamine and gentamycin. The biopsies were carefully cut up in a tissue culture device using forceps and a surgical blade in a laminar air current in sterile 6 cm plastic dishes. Then 3 ml of DMEM, containing 20% FCS, 2 mM glutamine and antibiotics were added and the culture was placed in an incubator at 37° C. After 10 days the medium was replaced by DMEM containing 10% FCS. Then the medium was changed a further 2 times a week. 4 weeks after the start of cultivation the cells which had grown out of the tissue fragments were trypsinised and plated out into new culture dishes for transfection.

An alternative preferred method consisted in transferring the skin fragments into fresh medium after cutting up and washing them once or twice with medium as required. 5 to 10 tissue fragments were placed in a T25-tissue culture flask the surface of which had been wetted with DMEM plus 10% FCS and were uniformly distributed, after which the flask was rotated. This caused the biopsies to hang down ("hanging drop configuration"; this method was described by Jones in 1989). After 1 to 3 hours in the incubator the flasks were turned again and filled with 1 to 2 ml of medium. Any fixed biopsies were topped up to 5 ml after 24 hours; otherwise, the process was repeated. After 6 to 10 days the first fibroblasts grew out and from this time on the medium was changed once a week. As soon as the cells were confluent they were transferred into a T75 flask.

h) Culture of Fibroblasts on PolyHEMA-coated Cell Culture Plates

The plates were coated with PolyHEMA (poly(2-hydroxy-ethyl-methacrylate)) by placing 200 µl of a Poly-HEMA solution (Sigma, Cat.No. P-3932; 10 mg/ml in 95% ethanol) in each well of a 24-well dish. The alcohol was allowed to evaporate off overnight at 37° C. and this process was repeated once more. After the second coating had dried the dishes were washed twice with HBS and once with medium before the cells were placed on it (Method A).

The culture dishes used for the experiments shown in FIG. 6 were prepared using a method similar to the one described by Folkman and Moscona, 1978. In order to do this, normal tissue culture plates (24-well plates) were coated with 200 µl of PolyHEMA solution in alcohol per well. After evaporation of the alcohol overnight at 37° C. the process was repeated. The values given in the Figure ($10^{-1}$, $10^{-2}$, $10^{-3}$) indicate the dilutions of the original PolyHEMA parent solution (6 g PolyHEMA in 50 ml of 95% ethanol) (Method B).

i) Luciferase Assay

The luciferase activity was determined as described in WO 93/07283.

j) Cytokine ELISAs

The Il-6-ELISA was obtained from R&D Systems and the IL-8-ELISA was obtained from Bender MedSystems.

k) LPS Preparation

A commercially obtainable LPS preparation from *Escherichi coli* (0111:B4, Sigma) was used. The preparation was dissolved in LPS-free water in a quantity of 10 mg/ml and before the preparation of serial dilution in LPS-free water it was sonicated for 5 minutes (SONOREX bath, 360 W). The final dilutions were sonicated for 5 minutes before use.

EXAMPLE 1

Activation of NF-IL-6 and NF-κB by the Introduction of Adenovirus

Stable clones of the lung epithelial carcinoma cell line A549 were produced, which contained pNF-κB-luc or pIL-6-luc as reporter gene construct. With these two cell lines (hereinafter also referred to as "A549 NF-κB cells" or "A549 IL-6 cells") the stimulatory behaviour of various agents was tested as follows: a defined number of cells were plated out ($4 \times 10^4$ cells per well in a plate having 24 wells for the A549-NF-κB cells; $4 \times 10^5$ cells per well of a plate with 6 wells for the A549-IL-6 cells) and 24 to 48 hours later exposed to the test agents for 4 hours in 2% equine serum/DMEM. The cells were then added to fresh medium (10% FCS/DMEM) and harvested for luciferase analysis (triple measurement) at the times specified in Table 1 (contents of 2 to 3 wells per sample). The control cells, harvested at the same times, were exposed to the same changes of medium, except that the test agents were missing.

The activation characteristics of each of these reporter cells and the concentration of the test substances are shown in Table 1 (when treated with adenovirus/pL/DNA as stimulus, the A549 NF-κB cells were treated with 20 µl of transfection complex ($4 \times 10^8$ virus particles, corresponding to $10^4$ viruses per cell) and the A549 IL-6 cells were treated with 200 µl of transfection complex, which again corresponded to $10^4$ viruses per cell).

In order to determine the time sequence of the NF-IL-6- and NF-κB-activation, the cells of the two cell lines which were found in the above quantities in a 24 well plate or 6 well plate were each treated with $10^4$ adenovirus dl1014 virus particles per cell (which corresponded to $4 \times 10^8$ virus particles for each well of the A549 NF-κB cells or $4 \times 10^9$ virus particles for each well of the A549 IL-6 cells). The time sequence of induction is shown in FIG. 1: the IL-6 promoter is fully activated after 12 hours and then rapidly returns to its original level, whilst the NF-κB promoter is activated and remains active for at least 50 hours. The latter finding conflicts with the published activation profile of NF-κB itself which, after activation, reverts to its original level after 6 to 12 hours as a result of the activation of the IκB synthesis (Sun et al., 1993; Scott et al., 1993; Chiao et al., 1994). (A possible explanation for this is that the synthetic NF-κB promoter used lacks the necessary inhibitory elements which ensure downward regulation, whilst the IL-6 promoter, a natural sequence, has the sequences which permit functioning of the normal control functions.)

EXAMPLE 2

Blocking the Activation of NF-κB by Expression of VA1

In this Example, investigations were carried out as to whether the introduction of a VA1 gene blocks the activation of NF-κB which is triggered by the introduction of transfection complexes of adenovirus/polylysine/DNA. In order to do this, $4\times10^4$ A549 NF-κB test cells per well of a 24 well plate were treated with $4\times10^8$ psoralen/UV-inactivated adenoviruses dl1014, corresponding to $10^4$ virus particles per cell, or with the corresponding number of viruses as constituent of the transfection complexes, corresponding to 20 µl of transfection complex, and it was found that a similar activation of NF-κB was caused (up to 6 to 7-fold after 72 hours). The incorporation of a DNA coding for E1B in the transfection complex (500 µl of the complex mixture contained 6 µg of pCMVE1B-DNA) had no effect on the inactivation of NF-κB. By contrast, the expression of the adenovirus-VA1 gene (caused by incorporation of the DNA coding for VA1 in the transfection complex; 500 µl contained 6 µg of pXVAH) reduced the activation to about 1.5 times the base level (FIG. 2; complex denotes pSP65, Complex/E1B denotes pCMVE1B, complex/VA1 denotes pXVAH).

EXAMPLE 3

Blocking the Activation of the IL-6 Promoter by Expression of VA1

The promoter for the human IL-6 gene contains binding sequences for the transcription factors NF-IL-6 and NF-κB which cooperate during activation of this promoter (Matsusaka et al., 1993; Betts et al., 1993).

A549 IL-6 cells were used which contain the luciferase gene under the control of the IL-6 promoter (NF-IL-6-luc) (each sample was in a well in a 6-well plate each containing $4\times10^5$ cells. Double measurements were carried out). Apart from the control samples in which only a change of medium was carried out (sample 1) the cells were treated with PMA (Phorbolmyristylacetate; $10^{-8}$M; sample 2), $10^4$ adenovirus particles contained in 200 µl of transferrin-polylysine/DNA complex which contained pSP65 as DNA (sample 3) or with $10^4$ virus particles contained in 200 µl of TfpL/DNA complex which contained pXVAH as DNA (sample 4) and after 10 hours the luciferase activity was measured as an indication of IL-6 activation. The results of the experiments were shown in FIG. 3.

EXAMPLE 4

Partial Inhibition of the Secretion of IL-6 and IL-8 in Human Skin Fibroblasts, Stimulated by the Entry of Adenovirus, by the Expression of VA1

After it had been demonstrated that the entry of virus stimulates both a promoter responding to NF-κB and also the IL-6 promoter responding to NF-κB/NF-IL-6 (Table 1, FIGS. 1, 2 and 3), the production of IL-6 and IL-8 by transfected primary fibroblasts was analysed as a measurement of the activation of the two endogenous genes which respond to NF-κB/NF-IL-6.

For this purpose, primary human fibroblasts ($2\times10^4$ cells per well) were treated either with $10^3$ of $3\times10^3$ psoralen/UV-inactivated adenovirus dl1014 particles per cell, incorporated in StpL/TfpL/DNA transfection complexes (corresponding to 2 µl or 6 µl of transfection complex, the DNA used either being an empty plasmid (pSP65; Boehringer Mannheim) or the plasmid designated pXVAH which contains the adenovirus VA1 sequence. The cells were treated for 4 hours with the transfection complexes in 2% equine serum/DMEM, then the medium was eliminated and replaced with 10% FCS/DMEM. After 24 hours (for IL-6) or 48 hours (for IL-8) aliquots of the medium were removed and investigated for their content of IL-6 or IL-8 using ELISA. It was found that treatment with the transfection complexes stimulates both IL-6 and IL-8 secretion by these cells (Table 2). In every case, the incorporation of the VA1 gene in the transfection complexes reduced the amount of cytokine produced by about 35%. The initial stimulation of cytokine production (entry of virus) must take place before the gene with the protective effect is introduced and is transcribed into active RNA. Therefore measurements of cytokine production were carried out at later times after transfection in order to determine whether the VA1 transfected cells exhibits a more marked suppression of cytokine production if higher concentrations of VA1-RNA have been formed.

EXAMPLE 5

Reduction in Gene Expression by Expression of the Adenovirus Genes E1A and E1A13S. Intensification of Gene Transfer by the Expression of E1B, E1B 19K and Bcl-2

First of all, a series of experiments were carried out intended to establish whether the expression of certain adenovirus genes is capable of intensifying gene expression after transferrinfection. A defined quantity of the luciferase expression plasmid pCMVL (5 µg) was mixed with various plasmid DNA (1 µg in each), incorporated in TfpL/StpL/adenovirus transfection complexes (total volume 500 µl) and applied to primary human fibroblasts (50 µl of complex were applied to $2\times10^4$ cells per well in a 24-well plate, corresponding to $2.5\times10^4$ virus particles per cell, the measurements being carried out three times. In FIG. 4 "minus" denotes pSP65; the test DNA is specified in each case). The luciferase activity obtained was measured 48 to 72 hours after transfection. The incorporation of purified total DNA of the E4-negative, E1-positive adenovirus dl1014 produced a two-fold increase in gene expression (FIG. 4). It was assumed that the increase can be attributed to the E1 expression. Then an E1 expression plasmid (pE1pAALM) was introduced together with the reporter plasmid into the cells and it was found that this also increases the gene expression (3-fold). The E1 region contains two main gene functions, E1A and E1B. (The E1A products have the effect of separating E2F from the Rb protein and on the other hand they modulate the transcription activity of numerous cellular and adenovirus promoters. The main transcription-transactivator function is contained in the 13S gene product. The 1B gene codes for two main functions: the EBB 55K gene product binds p53 and changes its function. It is assumed that the 19K E1B gene product acts underneath p53 in order to block the apoptotic response).

The co-expression of plasmids which carry either the complete E1A or the complete E1B region under the control of the CMV promoter was tested. The E1B plasmid gave a 7-fold increase in gene expression. By contrast, the E1A plasmid led to an inhibition of gene expression (0.3 times that of the control sample). The 19K E1B gene also resulted in an increase in gene expression (8.6 fold).

The E1B 19K protein was recently shown to be a highly effective analogue of the anti-apoptotic gene Bcl-2 (Rao et al., 1992). Therefore, Bcl-2 was also tested and was found to bring about a 5.5 fold increase in gene expression.

EXAMPLE 6

Investigation of the Toxicity on Specificity

Next, tests were carried out to find out whether the decrease in gene expression could be attributed to a nonspecific toxicity caused by the high virus/cell ratios (the experiments were carried out with about 50,000 virus particles per cell).

In order to do this, transfection complexes containing pCMVL plus the plasmid pSP6S, or the plasmids which contained the sequence for Bcl-2, E1A or E1B 19K (the quantities of reporter plasmid pCMVL and the relevant test plasmid were 5 µg and 1 µg, respectively, as in the previous Example), with virus particle numbers of $3 \times 10^4$ (FIG. 5A), $10^4$ (FIG. 5B) or $3 \times 10^3$ (FIG. 5C) per cell were applied to primary fibroblasts and the luciferase activity was measured over a period of time. The transfections were carried out as described in the preceding Examples, the cells being given 6, 18 or 60 µl of transfection complex per well, containing $2 \times 10^4$ fibroblasts. The results of the experiments are shown in FIG. 5: similar gene expression patterns were obtained to those in the preceding Examples (decrease in E1A-treated cells, increase in 19K- and Bcl-2-treated cells), irrespective of the dosage of virus used.

In the preceding Example, a loss in expression activity was found at later times, particularly after 6 days, even in the cells transfected with 19K or Bcl-2. Therefore, some thought was given as to whether a second phenomenon connected with the inflammatory response as demonstrated in the preceding Example might be affecting the health of the transfected culture. If the transfected cells exhibit activation of the immune response as a result of the transfection process, the secretion of cytokines or toxins by the cells could restrict the life expectancy of the culture.

In order to investigate this phenomenon, experiments were carried out into the progress of transfection over time, using transfection complexes containing 5 µg of pCMVL plus 1 µg of pSP65 or 1 µg of a plasmid containing E1A, E1A 13S, E1B 19K or Bcl-2. (In these experiments, the cells in a well were given 18 µl of transfection complex.) From day 10 onwards, the culture medium was replaced with fresh medium daily; the idea of this procedure was to lower the concentrations of toxins by changing the medium. The results of these experiments are given in FIG. 6: it was found that the procedure chosen increased the long-term gene expression of the cultures when pSP65, Bcl-2 or 19K plasmids were used. By contrast, the expression of the E1A- and E1A-13S cultures decreased to a degree similar to that of the unwashed cultures in the preceding experiments. The presence of 19K showed an improvement in gene expression by a power of ten, even after 21 days, which indicates the involvement of apoptosis.

EXAMPLE 7

Investigation into the Morphology of Transfected Cells

Primary human fibroblasts were transfected with the reporter plasmid pCMVβgal plus pSP65 or plus pCMV19K ($2 \times 10^4$ fibroblasts per well of a 24-well plate were given 18 µl of transfection complex; 500 µl of complex contained either 4 µg of pCMVL plus 2 µg of pSP65 or 4 µg of pCMVL plus 2 µg of pCMV19K). 48 hours after transfection the cells were stained with X-gal described in WO 93/07283 in order to investigate the morphology of the cells which had successfully absorbed and expressed the transfected DNA. It was found that, at this early stage after transfection, both cell populations expressed the transfected cell within one order or magnitude. However, whereas the β-gal expressing cells exhibit a predominantly rounded and partly detached morphology in the absence of pCMV19K (FIG. 7, left-hand Table) which agrees with an apoptotic phenotype, the cells co-transfected with pCMV19K displayed a predominantly flat and adhering morphology (FIG. 7, right-hand Table). The change in morphology would appear to be connected with the more extended and intensified gene expression achieved with 19K.

EXAMPLE 8

Inhibition of the Toxicity Caused by Adenovirus or LPS by Pre-expression of E1B 19K and Bcl-2

In the course of preliminary tests in which the cells were exposed to LPS in the presence of adenovirus, it was found that the rapidly occurring toxicity in these cells causes morphology of the dying cells which is similar to apoptosis (e.g. fragmented nuclei, condensation). It was then assumed that the penetration of LPS into the cell causes an apoptotic response during the entry of adenovirus.

In order to investigate this phenomenon, transfection complexes were prepared, containing LPS plus either E1B 19K gene or Bcl-2 gene, in order to find out whether the total introduction of the apoptosis initiator LPS with the anti-apoptosis gene Bcl would block cell death. It was found that there is no reduction in toxicity, presumably because the speed of the toxic response, which is apparent 4 hours after treatment, does not allow sufficient 19K- or Bcl-2-gene product to accumulate. In the light of this observation an alternative method was developed for establishing whether 19K or Bcl-2 could confer protection from the LPS-induced toxicity: stable cell lines which carried either the 19K- or the Bcl-2-gene were brought into contact with the LPS/adenovirus complexes. In order to do this, A549 cells as control cells and A549 19K cells and A549-Bcl-2 cells were plated out in amounts of $4 \times 10^4$ cells per well of a 24-well plate and treated with 50 µl of transfection complex containing 6 µg pCMVL per 100 µl of complex and either 0, 10 or 100 ng of LPS per 6 µg of DNA. The expectation that the preceding expression of each of these proteins would have a protective effect proved correct: as shown in FIG. 8, control cells which were exposed to the adenovirus/pL/DNA complexes were killed as a function of the increasing LPS content in the sample (cf. sample 1: no LPS, with samples 2 and 3: 10 and 100 ng LPS/6 µg of DNA). In cells which express either 19K or Bcl-2, there was a reduction in toxicity to 39% (sample 2) or 77 or 60% (sample 5 or 8; 19K or Bcl-2). When evaluating these results it should be noted that the cells examined in this experiment were still pools of stably expressing cells; pure populations of 19K or Bcl-2 expressing cells can be expected to have a greater protective effect (up to 100%).

EXAMPLE 9

Increase of Gene Transfer by the Glucocorticoid Dexamethasone on Its Own or in Conjunction with an Anti-apoptosis Gene Primary human fibroblasts were transfected with adenovirus/polylysine/DNA complexes as described in Example 5, using as DNA either pCMVL/pSPG5 or pCMVL/pCMV19K in a ratio of 5:1. 4 hours after transfection the samples were transferred into fresh 10% FCS/DMEM medium or into 10% FCS/DMEM medium containing 3 µM of dexamethasone (Sigma). 24 hours after transfection the samples (double measurement) were harvested and the luciferase activity was determined. It was found that the presence of dexamethasone in the absence of pCMV19K increases the luciferase expression by a factor of 1.65. In the presence of both dexamethasone and pCMV19K the increase in 5,8,11-eicosatriynoic acid was 2.71-fold (Table 3).

The further progress over a period of 7 days is shown in FIG. 9; the medium containing dexamethasone was changed every two days. At each of the given times, double measurements of the luciferase activity were made.

EXAMPLE 10

Investigation of the Effect of Inhibitors of Arachidonic Acid Metabolites on Gene Expression In order to find out whether arachidonic acid metabolites are involved in reducing gene expression in transfected cells, primary skin fibroblasts were transfected with adenovirus/polylysine/DNA complexes containing the luciferase gene, as described in the preceding Examples, both with and without co-transfection of the E1B 19K gene, and the luciferase activity was monitored over a period of time. (The DNA contained 5.5 µg of pCMVL and 0.5 µg of pSP65 (control) or pCMV19K). 2 hours after transfection the cells were transferred into standard medium (DMEM plus 100 FCS) containing 10 µM of dexamethasone or 2 mM of Aspirin, where shown in FIG. 10. Triple measurements were carried out. The results of these experiments were shown in FIG. 10. It was found that both dexamethasone and aspirin bring about an increase in gene expression both in the presence and in the absence of E1B 19K. The effect of aspirin was less marked than that of dexamethasone, which indicates that the inhibition of cyclooxygenase is not sufficient to prevent the decline in gene expression. Both substances exhibited a synergistic effect with the E1B 19K gene, in terms of the increase in gene expression.

EXAMPLE 11

Comparison of the Effect of Dexamethasone, Ibuprofen and 5,8,11-eicosatriynoic Acid in the Presence or Absence of E1B 19K Analogously to the method described in the preceding Example, transfections were carried out and the luciferase expression was measured. 2 hours after transfection, in this experiment as well, the cells were placed in standard medium which contained, where shown in FIG. 11, 10 µM of dexamethasone, the cyclooxygenase inhibitor ibuprofen (100 µM) or the 5-lipoxygenase inhibitor 5,8,11-eicosatriynoic acid (30 µM); the optimum concentrations of the inhibitors had each been determined by titration in preliminary tests. The results of these tests are shown in FIG. 11. It was found that, of the three anti-inflammatory substances investigated, only dexamethasone brings about a substantial improvement in gene expression in the absence of E1B 19K. In the presence of E1B 19K a synergistic effect is observed between dexamethasone and 5,8,11-eicosatriynoic acid.

EXAMPLE 12

Comparison of the Increase in Gene Expression Brought About by Various Inhibitors of Arachidonic Acid Metabolites As described in the previous Examples, transfections were carried out and the luciferase expression was measured. The inhibitors used were dexamethasone (10 µM), 5,8,11-eicosatriynoic acid (30 µM), NDGA (10 µM), ibuprofen (30 µM) and aspirin (2 mM). In FIG. 12 the arachidonic acid pathway is shown on the left, the inhibitors are shown in the centre at the various points of their activity and on the right the expression values obtained are given. Whereas all the inhibitors investigated showed a certain improvement in gene expression which might possibly be attributable to an improvement in the condition of the cells as a whole, the clearest improvement was found with dexamethasone treatment. This could be due to the fact that this glucocorticoid acts at numerous points (dexamethasone is capable of blocking the gene expression of inflammatory cytokines by acting as a negative transcription modulator (e.g. in order to block the IL-6 gene); however, it may also act by reducing the phospholipase mRNA concentration or by increasing the lipocortin concentrations (Barnes and Adcock, 1993).

EXAMPLE 13

Identification of an Anti-apoptotic Gene of Chicken Adenovirus CELO (Chicken Embryo Lethal Orphan)

a) Isolation and Cloning of CELO Virus Genome Fragments

The starting material used was the CELO virus adenovirus type 1 (ATCC VR-432). The virus was purified after growth in chicken embryos as described by Cotten et al., 1993. The DNA was extracted from the virus by incubating the virus with proteinase K (0.3 mg/ml) in HBS/0.1% SDS for 45 minutes at 56° C. Then CsCl was added (28.5 g/26 ml of solution), followed by ethidium bromide (0.1 mg/ml) and the sample was centrifuged for 18 hours in a Vti 65 rotor (Beckman, 20° C.). The DNA (clearly visible stained band) was collected, the ethidium bromide was extracted by extraction with CsCl-saturated isopropanol until the pink coloration disappeared and the CsCl was removed by gel filtration.

The entire 42.8 kb CELO virus genome obtained was digested on the one hand with EcoRI and on the other hand with HindIII. The mixture of fragments obtained was resolved in a 0.8% agarose gel and purified on a 3 mm Whatman paper and subsequently over a Sephadex G-50 column.

The restriction map of CELO virus is shown at the top of FIG. 13; it is based on the restriction maps of Cai and Weber, 1993; Alestrom et al., 1982, and Li et al., 1984. The Figure shows the position of the HindIII and EcoRI sites (in mapping units, one mapping unit being 428 base pairs). The nomenclature of the expression clones and the position of the fragments 7H3 (HindIII D-fragment) and 9R1 (EcoRI D-fragment) are also shown. These fragments are those which displayed a positive effect in the gene transfer experiments (cf. the experiments described in b).

The fragments obtained were cloned in the expression vector pX described by Superti-Furga et al., 1991, downstream from the CMV Immediate Early Promotor, each fragment being isolated and characterised in both orientations.

b) Testing of the Isolated Gene Fragments for Anti-apoptotic Effect

In order to establish whether the expression of the gene fragments obtained is capable of reducing the decline in gene expression which occurs during transferrinfection, transfection tests were carried out as described in Example 5, the test plasmids containing the various CELO virus fragments specified in FIG. 16. The quantity of transfection complexes was 15 µl per 20,000 cells, containing 5 µg of luciferase reporter plasmid and 1 µg of the test plasmid (in most cases, clones containing the fragment in both directions relative to the promoter were tested). The values for gene expression obtained for the various clones (measurements were taken after 24 hours and then on day 4, 7, 14 and 21) in relation to the control value are shown in FIG. 16, in which the HindIII fragments are marked "H3" and the EcoRI fragments are marked "R1".

In every case the luciferase expression was similar after 24 hours; on the 4th day there was a noticeable reduction in the expression of the controls. FIG. 16 shows the relative expression (mean of 3 samples) of the test samples (5 μg of luciferase reporter plasmid and 1 μg of plasmid pXCELO) compared with the control samples (5 μg of luciferase reporter plasmid pCMVL and 1 μg of empty vector) on day 14. A protective effect (three-fold to eight-fold increase in luciferase expression) could be observed only in the plasmids which contained the 7H3- and 9R1-fragments; these two fragments originate from the same region of the CELO virus genome and have an overlapping area of about 80% in their sequence (see the restriction map shown in FIG. 13).

The DNA sequences of fragments 9R1 and 7H3, which had demonstrated a protective effect, were measured by standard methods. In order to do this, DNA fragments were subcloned in pBSII (Stratagene), by combining Exo III and Si nuclease deletions were carried out from one direction, clones were isolated and sequenced on an ABI 373 sequence analyser using the "Taq-Dye-Deoxy Terminator Cycle Sequencing system" (ABI). Clones of the reverse orientation were sequenced using synthesised primers.

Analysis of the open reading frames coded by the two fragments 9R1 and 7H3 yielded a single larger open reading frame common to both fragments (shown at the bottom of FIG. 13; the open reading frame marked with an * denotes the large open reading frame common to 9R1 and 7H3). This open reading frame, the sequence of which is underlined in FIG. 14, codes for a protein with 283 amino acids, beginning with nucleotide 577. The corresponding gene product was designated GAM-1.

FIG. 17 shows the open reading frames, which are larger than 200 base pairs, obtained after sequence analysis using the automatic fluorescence dideoxy method, as black bars; the SmaI/HindIII fragment, of which only the relevant restriction sites which occur only once are shown, proved in the tests described in the following Example to have a full activity).

Larson et al., 1986 identified a VA gene in the CELO virus in the gene fragment between mapping units 88.7 and 92.7. This VA gene (in the 9R1 sequence of nucleotide 4286-4184) was reported to increase the gene expression of co-transfected genes to a small degree. Since this gene is admittedly present in the 9R1 fragment but lies outside the 7H3 fragment, it cannot be assumed that it contributes to the effect of increasing gene expression observed in the present experiments and situated in this region. In order to establish whether this increasing effect is a new function of the open reading frame of 9R1 and is not connected with the VA function described above, an SmaI/HindIII restriction fragment of 9R1 was prepared which contains the open reading frame of 9R1 but not the VA gene. Therefore, analogously to the transfection with the 7H3 and 9R1 fragments, transfections were also carried out with this restriction fragment (9R1S/H3) which had also been cloned in the pX vector. The results of these transfections showed that the increasing effect of the fragment on gene expression is not a function of the VA gene.

c) Progress of Gene Expression in the Presence of the Fragments 7H3, 9R1 and 9R1S/H3

In order to carry out a more detailed investigation into the increase in gene expression, transfections were carried out with the 9R1 fragment, the 7H3 fragment and the SmaI/HindIII fragment of 9R1 and the luciferase expression was monitored over a lengthy period. (The transfection complexes contained 5 μg of pCMVL and either 1 μg of pSP65 as control or 1 μg of the vector pX with the fragment in question). It was found that the maintaining of gene expression with the fragments 9R1, 7H3 and the 9R1S/H3 construct is comparable, which leads one to conclude that the protective effect of 9R1 and 7H3 is wholly contained in the SmaI/HindIII fragment of 9R1. These experiments indicate that the active gene is defined by the open reading frame of this region. The results of these experiments are shown in FIG. 15.

d) Effect of Mutations on the Anti-apoptotic Activity of GAM-1

Primary human fibroblasts were transfected as described in the preceding Examples, with a luciferase plasmid and the empty vector pX (control) or with the various test plasmids (5.5 μg of pCMVL plus 0.5 μg of test plasmid), the test plasmids containing the mutated sequences.

In view of the restriction map of the 9R1 fragment and in the light of the observation that the expression-increasing activity occurs with both 9R1 and 7H3, it could be assumed that this activity must be situated to the left of the single HindIII site of the 9R1 fragment. A SmaI/HindIII restriction site contains the largest open reading frame to the left of the HindIII site. When this fragment was subcloned into a vector, it was found that it contains all the activity of the 9R1 fragment (FIG. 18, column 4).

BssHII cuts above the open reading frame, which is presumed to be active. Cutting with BssHII, treatment with Klenow/T4-DNA polymerase to remove the overhanging nucleotides and religating the SmaI/HindIII fragment introduces a stop codon above this reading frame and should not therefore affect the activity of the gene obtained. This assumption was confirmed (FIG. 18, column 4); thus, the activity is clearly outside the BssHII region. Similar treatments (restriction digestion/Klenow/T4-DNA polymer and religation) at three other restriction sites (SacII, SphI and BglII) of the presumed open reading frame destroyed the protective effect (FIG. 18, columns 5, 6, 7): all these treatments introduce stop codons within the presumed reading frame and would therefore shorten the resulting proteins in the region of the relevant restriction sites (the precise protein sequences (in single letter code) and the activity of the mutants are given in Table 4).

In order to test the effect of mutations in the leucine zipper, two of the leucine groups in the GAM-1 zipper were mutated by PCR into proline groups (GAM-1 mutant #6; L258P, L265P). Primary human fibroblasts were transfected again as described above, with 5 μg of pCMVL plus 1 μg of the test plasmid given in FIG. 19, except in the case of sample 4, where 0.5 μg of E1B 19 K and 0.5 μg of p9R1 S/H3 (=SmaI/HindIII fragment of 9R1) were used. The luciferase expression was measured 4 days after transfection. It was found that the introduction of these point mutations destroys the protective effect of GAM-1 (FIG. 19, column 5).

EXAMPLE 14

Effect of GAM-1 on Cell Death Caused by the Detachment of Cells from the Substrate ("Detachment-induced Apoptosis")

a) Effect of Different GAM-1 Fragments

Primary human fibroblasts were transfected, as in preceding Examples, with a luciferase reporter plasmid and either with the empty vector pSP65 (control) or with the various test plasmids (pXCELO) which contained the fragment given in FIG. 20 (5 µg of pCMVL plus 1 µg of the test plasmid in question). 2 days after transfection the cells were trypsinised, counted, and a defined number of cells (20,000 per well) were plated in 24-well plates (3-fold) which had been coated with polyHEMA using method A. 7 days after plating out the luciferase activity of the entire population (both non-adhering and adhering cells) was measured. Each of the values given in FIG. 20 is the average of 3 transfections).

b) Comparison of the Effect of GAM-1 with E1B 19 K and Bcl-2

Primary human fibroblasts were transfected as in the preceding Examples with a luciferase reporter plasmid and either with the empty vector pSP65 (control) or with the various test plasmids (5 µg of pCMVL plus 1 µg of pSP65 or pE1B 19K, pBCL-2 or p9R1 S/H3). 2 days after transfection the cells were trypsinised and counted and a defined number of cells (20,000 per well) were plated out (3-fold) either in normal 24-well plates or in 24-well plates coated with PolyHEMA using method B. FIG. 21 gives the dilution of the PolyHEMA used for the coating. 7 days after plating out, the luciferase activity of the entire cell population (both non-adhering and adhering cells) was measured. Each of the values shown in FIG. 21 is the average of 3 transfections.

EXAMPLE 15

Effect of the Combination of GAM-1 with E1B 19K or with Bcl-2

Primary human fibroblasts were transfected as in the previous Examples with a luciferase reporter plasmid and either with the empty vector pSP65 (control) or with the various test plasmids specified in FIG. 22 (5 µg pCMVL plus 1 µg of the relevant test plasmid in samples 1 to 4, in samples 5 and 6 the mixture contained 0.5 µg of the test plasmid in addition to the reporter plasmid). FIG. 22 shows the luciferase expression 22 days after transfection, each value being the average of 3 transfections.

TABLE 1

| Cell type | Stimulus | Concentration | Increase (-fold) |
|---|---|---|---|
| A549/NF-KB | LPS | 2.5 µg/ml | 1.3 (11 h) |
| | PMA | $10^{-8}$ M | 2.0 (11 h) |
| | Adenovirus | $10^4$ Particle/cell | 4.2 (72 h) |
| | Adenovirus + LPS | $10^4$ Particle/cell + 2.5 µg/ml | 4.9 (72 h) |
| | Adenovirus (Psor) | $10^4$ Particle/cell | 3.4 (72 h) |
| | Adenovirus (Psor) + LPS | $10^4$ Particle/cell + 2.5 µg/ml | 2.9 (72 h) |
| | Adenovirus (Psor)/ pL/DNA | $10^4$ Particle/cell | 10.0 (48 h) |
| A549/NF-IL-6 | PMA | $10^{-8}$ M | 2.0 (10 h) |
| | Adenovirus (Psor) | $10^4$ Particle/cell | 2.3 (10 h) |
| | Adenovirus (Psor)/ pL/DNA | $10^4$ Particle/cell | 3.1 (48 h) |

Psor = Psoralen/UV-inactivated

TABLE 2

| Cells | Stimulus | |
|---|---|---|
| | | IL-6 (pg/$10^6$ cells) |
| primary Fibroblasts | $10^3$ Adenovirus dl1014 | 4000 |
| | $10^3$ Adenovirus dl1014 + VA1 | 2500 (37.5% reduction) |

TABLE 2-continued

| Cells | Stimulus | |
|---|---|---|
| | $3 \times 10^3$ Adenovirus dl1014 | 9500 |
| | $3 \times 10^3$ Adenovirus dl1014 + VA1 | 6000 (37% reduction) |
| | | IL-8 (pg/$10^6$ cells) |
| primary Fibroblasts | $10^3$ Adenovirus dl014 | 500 |
| | $10^3$ Adenovirus dl1014 + VA1 | 100 (80% reduction) |
| | $3 \times 10^3$ Adenovirus dl1014 | 3700 |
| | $3 \times 10^3$ Adenovirus dl1014 + VA1 | 2400 (35% reduction) |

TABLE 3

| Conditions | Induction (-fold) |
|---|---|
| pCMVL/pSP65 | 1.0 |
| pCMVL/pSP65/Dexamethasone | 1.65 |
| pCMVL/pCMV19K | 1.0 |
| pCMVL/pCMV19K/Dexamethasone | 2.71 |

TABLE 4

| Construct | Properties | Activity |
|---|---|---|
| 9R1 SmaI/HindIII | Wild-type sequence | + |
| Mutant BssHII | Wild-type sequence | + |
| Mutant SacII | Wild-type to S93 Addition of GTQDPQstop | − |
| Mutant SpHI | Wild-type to V145 Addition of Pstop | − |
| Mutant BglII | Wild-type up to D195 Addition of RSEKNTSRTILQPIFstop | − |
| Mutant #6 (L258P, L265P) | Changes L258 into P Changes L265 into P | − |

LITERATURE

Ackrill, A. M., Foster, G. R., Laxton, C. D., Flavell, D. M., Stark, G. R. and Kerr, I. M., 1991, Nucleic Acids Res. 19, 4387–4393.

Alestrôme, P., Stenlund, A., Li, P., Bellet, A. and Petterson, U., 1992, J. Virology 42, 306–310.

Barber, A. E., Coyle, S. M., Marano, M. A., Fischer, E., Calvano, S. E., Fong, Y., Moldawer, L. L. and Lowry, S. F., 1993, J. Immunol. 150, 1999–2006.

Barnes, P. J. and Adcock, I., 1993, Trends in Pharm. Sci. 14, 436–441.

Behr, J. P., Demeneix, B., Loeffler, J. P. and Perez-Mutul, J., 1989, Proc.Natl.Acad.Sci. USA 86, 6982–6986.

Betts, J., Cheshire, J., Akira, S., Kishimoto, T. and Woo, P., 1993, J. Biol. Chem. 268, 25624–25631.

Boehmelt, G., Walker, A., Kabrun, N., Mellitzer, G., Beug, H., Zenke, M. and Enrietto, J. P., 1992, EMBO J. 11, 4641–4652.

Bridge, E. and Ketner, G., 1989, J. Virol. 63, 631–638.

Brooks, P. C., Montgomery, A. M. P., Rosenfeld, M., Reisfeld, R. A., Hu, T., Klier, G. and Charesh, D. A., 1994, Cell 79, 1157–1164.

Burkart, V. and Kolb. H., 1993, Clin. Exp. Immunol. 93, 273–8.

Busch, S. J. and Sassone-Corsi, P., 1990, Trends in Genetics 6, 36–40.

Cai, F. and Weber, J. M., 1993, Virology 196, 358–362.

Chen, C.-Y., Oliner, J. D., Zhan, Q., Fornace, A. J., Vogelstein, B. and Kastan, M. B., 1994, Proc.Natl.Acad. Sci. USA 91, 2684–2688.

Chiao, P. J., Miyamoto, S. and Verma, I. M., 1994, Proc. Nat.Acad.Sci. USA 91, 28–32.

Cifone, M. G., Botti, D., Festuccia, C., Napolitano, T., del-Grosso, E., Cavallo, G., Chessa, M. A. and Santoni, A., 1993, Cell. Immunol.148, 247–58.

Clarke, P. A., Sharp, N. A. and Clemens, M. J., 1990, Eur. J. Biochem. 193, 635–641.

Clarke, P. A., Schwemmle, M., Schickinger, J., Hilse, K. and Clemens, M. J., 1991, Nucleic Acids Res. 19, 243–248.

Clem, R. J. and Miller, L. K., 1994, in Apoptosis II: The Molecular Basis of Apoptosis in Disease. L. D. Tomei and F. O. Cope ed. Cold Spring Laboratory Press, Cold Spring Harbor, N.Y.

Conti, P., Panara, M. R., Barbacane, R. C., Bongrazio, M., Dempsey, R. A. and Reale, M., 1993, Clin. Exp.Immunol. 91, 526–31.

Cotten, M., Wagner, E., Zatloukal, K., Phillips, S., Curiel, D. T. and Birnstiel, M. L., 1992, Proc.Natl.Acad.Sci. USA 89, 6094–6098.

Cotten, M. and Wagner, E., 1993, Current Opinion in Biotechnology 4, 705–710.

Cotten, M., Wagner, E., Zatloukal, K. and Birnstiel, M. L., 1993, J. Virol. 67, 3777–3785.

Curiel, D. T., Agarwal, S., Wagner, E. and Cotten, M., 1991, Proc.Natl.Acad.Sci. USA 88, 8850–8854.

Curiel, D. T., Agarwal, S., Romer, M. U., Wagner, E., Cotten, M., Birnstiel, M. L. and Boucher, R. C., 1992a, Am.J.Respir.Cell and Mol.Biol. 6, 247–252.

Curiel, D. T., Wagner, E., Cotten, M., Birnstiel, M. L., Agarwal, S., Li, Ch.-M., Loechel, S. and Hu, P.-H., 1992b, Human Gene Therapie 3, 147–154.

Debbas, M. and White, E., 1993, Genes and Dev. 7, 546–554.

De Wet, J., Wood, K., DeLuca, M., Helinski, D. and Subramani, S., 1987, Mol. Cell. Biol. 7, 725–737.

D'Halluin, J., Allart, C., Cousin, C., Boulanger, P., and Martin, G., 1979, J. Virol. 32, 61–71.

Evan, G. I. et al., 1992, Cell 69, 119–128.

Ezoe, H., Lai Fatt, R. and Mak, S., 1981, J. Virol. 40, 20–27.

Felgner, J., Bennett, F. and Felgner, P. L., 1993, Methods 5, 67–75.

Flower, R. J., Moncada, S. and Vane, J. R., 1985, pp 674–715 in Goodman and Gilman's The Pharmacological Basis of Therapeutics. 7th Ed. Gilman Goodman, A., Goodman, L. S., Rall, T. W. and Murad, F. Eds. Macmillan Publishing Inc. New York.

Folkman, J. and Moscona, A., 1978, Nature 273, 345–349.

Gross, V., Villiger, P. M., Zhang, B. and Lotz, M., 1993, J. Leukoc. Biol. 54, 125–132.

Grosveld, F. et al., 1982, Nucleic Acids Res. 10, 6715.

Gunnery, S., Rice, A. P., Roberstson, H. D. and Mathews, M. B., 1990, Proc.Natl.Acad.Sci. USA 87, 8687–8691.

Gutch, M. J. and Reich, N. C., 1991, Proc.Natl.Acad.Sci. USA 88, 7913–7917.

Harroch, S., Revel, M. and Chebath, J., 1994, EMBO J. 13, 1942–1949.

Jones, G. E., 1989, Establishment, Maintenance and Cloning of Human Primary Cell Strains, Methods in Molecular Biology, Vol. 5.

Kasid, A., Morecki, S., Aebersold, P., Cornetta, K., Culver, K., Freeman, S., Director, E., Lotze, M. T., Blaese, R. M., Anderson, W. F. and Rosenberg, S. A., 1990, Proc.Natl.Acad.Sci. USA 87, 473–477.

Kédinger et al., 1984, Proc.Natl.Acad.Sci. USA 81, 4381–4384.

Kishimoto, T., Akira, S. and Taga, T., 1992, Science 258, 593–597.

Lai Fatt, R. and Mak, S., 1982, J. Virol. 42, 969–977.

Larson, S., Bellett, A., and Akusjärvi, G., 1986, J. Virol. 58, 600–609.

Lemay, P., Boudin, M., Milleville, M. and Boulanger, P., 1980, Virology 101, 131–143.

Levine, A. J., 1990, Virology 177, 419–426.

Levine, B., Huang, Q., Isaacs, J. T., Reed, J. C., Griffin, D. E. and Hardwick, J. M., 1993, Nature 361, 739–742.

Li, P., Bellett, J. D. and Parish, C. R., 1984, J. Virol. 52, 638–649.

Lim, K. and Chae, C. B., 1989, BioTechniques 7, 576–579.

Lumb, K. J. and Kim, P. S., 1995, Science 268, 436–439.

McCarthy, S. A., Symonds, H. S. and Van Dyke, T., 1994, Proc.Natl.Acad.Sci. USA 91, 3979–3983.

MacMillan, R. M. and Walker, E. R. H., 1992, Trends in Pharm Sci. 13, 323–330.

Manche, L., Green, S. R., Schmedt, C. and Mathews, M. B., 1992, Mol. Cell. Biol. 12, 5238–5248.

Massague et al., 1987, Cell 49, 437.

Mathews, M. B., and Shenk, T., 1991, J. Virol. 65, 5657–5662.

Matsusaka, T., Fujikawa, K., Nishio, Y., Mukaida, N., Matsushima, K., Kishimoto, T. and Akira, S., 1993, Proc.Natl.Acad.Sci. USA 90, 10193–10197.

Meredith, J. E., Fazeli, B. and Schwartz, M. A., 1993, Mol. Biol. of the Cell 4, 953–961.

Momand, J., Zambetti, G. P., Olson, D. C., George, D. and Levine, A. J., 1992, Cell 69, 1237–1245.

Moore et al., 1990, Science 248, 1230.

Mulligan, R. C., 1993, Science 260, 926–932.

Neilan, J. G., Lu, Z., Afonso, C. L., Kutish, G. F., Sussman, M. D. and Rock, D. L., 1993, J. Virol. 67, 4391–4394.

Oliner, J. D., Pietenpol, J. A., Thiagalingam, S., Gyuris, J., Kinzler, K. W. and Vogelstein, B., 1993, Nature 362, 857–860.

Pace, J., Hayman, M. J. and Galan, J. E., 1993, Cell. 72, 505–14.

Pasquale, D. and Chikkappa, G., 1993, Exp. Hematol. 21, 1361–5.

Pearson, G. R., Luka, J., Petti, L., Sample, J., Birkenback, M., Braun, D. and Kieff, E., 1987, Virology, 160, 151–161.

Pilder, S., Logan, J. and Shenk, T., 1984, J. Virol. 52, 664–671.

Rao, L., Debbas, M., Sabbatini, P., Hockenbery, D., Korsmeyer, S. and White, E., 1992, Proc.Natl.Acad.Sci. USA 89, 7742–7746.

Rao, G. N., Lassegue, B., Griendling, K. K. and Alexander, R. W., 1993, Oncogene. 10, 2759–64.

Ray, A., LaForge, S. and Sehgal, P. B., 1990, Mol. Cell. Biol. 10, 5736.

Ruoslahti, E. and Reed, J. C., 1994, Cell 77, 477–478.

Scott, M. L., Fujita, T., Liou, H. C., Nolan, G. P. and Baltimore, D., 1993, Genes Dev. 7, 1266–1276.

Sehgal, P., Helfgott, D., Santhanam, U., Tatter, S., Clarick, R. Ghrayeb, J. and May, L., 1988, J. Exp. Med. 167, 1951–1956.

Seto, M. Jaeger, U., Hockett, R. D., Graninger, W., Bennett, S., Goldman, P. and Korsmeyer, S. J., 1988, EMBO J. 7, 123–131.

Strijker, R., Fritz, D. T. and Levinson, A. D., 1989, EMBO J., 8, 2669–2675.

Subramanian, T., Kuppuswamy, M., Gysbers, J., Mak, S. and Chinnadurai, G., 1984, J. Biol. Chem. 259, 11777–11783.

Sugimoto, A., Friesen, P. D. and Rothman, J. H., 1994, EMBO J. 13, 2023–2028.

Sun, S. C., Ganchi, P. A., Ballard, D. W. and Greene, W. C., 1993, Science 259, 1912–1915.

Superti-Furga, G., Bergers, G., Picard, D. and Busslinger, M., 1991, Proc.Natl.Acad.Sci. USA 88, 5114–5118.

Svensson, C. and Akusjärvi, G., 1984, Mol. Cell. Biol. 4, 736–742.

Svensson, C. and Akusjärvi, G., 1990, Virology 174, 613–617.

Takemori, N., Cladaras, C., Bhat, B., Conley, A. and Wold, W., 1984, J. Virol. 52,793–805.

Vieira et al., 1991, Proc.Natl.Acad.Sci. USA 88, 1172.

Visvanathan, K. V. and Goodbourn, S., 1989, EMBO J. 8, 1129–1138.

Wagner, E., Zenke, M., Cotten, M., Beug, H. and Birnstiel, M. L., 1990, Proc.Natl.Acad.Sci. USA 87, 3410–3414.

Wagner, E., Cotten, M., Mechtler, K., Kirlappos, H. and Birnstiel, M. L., 1991, Bioconjugate Chemistry 2, 226–231.

Wagner, E., Zatloukal, K., Cotten, M., Kirlappos, H., Mechtler, K., Curiel, D. T. and Birnstiel, M. L., 1992, Proc.Natl.Acad.Sci. USA 89, 6099–6103.

Weinberg, D. H. and Ketner, G., 1983, Proc.Natl.Acad. Sci. USA 80, 5383–5386.

Wertheim, W. A., Kunkel, S. L., Standiford, T. J., Burdick, M. D., Becker, F. S., Wilke, C. A., Gilbert, A. R. and Strieter, R. M., 1993, J. Immunol. 151, 2166–2175.

White, E. and Cipriani, R., 1989, Proc. Natl. Acad. Sci. USA 86, 9886–9890.

White, E. and Cipriani, R., 1990, Mol Cell. Biol. 10, 120–130.

White, E., Grodzicker, T. and Stillman, B. W., 1984, J. Virol. 52, 410–419.

White, E. and Stillman, B., 1987, J. Virol. 61, 426–435.

White, K., Grether, M. E., Abrams, J. M., Young, L., Farrell, K. and Steller, H., 1994, Science 264, 677–683.

Wilson, J. M., Danos, O., Grossman, M., Raulet, D. H. and Mulligan, R. C., 1990, Proc.Natl.Acad.Sci. USA 87, 439–443.

Wu, G. Y, and Wu, C. H., 1987, J. Biol. Chem. 262, 4429–4432.

Wu, X. and Levine, A. J., 1994, Proc.Natl.Acad.Sci. USA 91, 3602–3606.

Zatloukal, K., Wagner, E., Cotten, M., Phillips, S., Plank, C., Steinlein, P., Curiel, D. and Birnstiel, M. L., 1992, Ann.New York Acad.Sci. 660, 136–153.

Zitnik, R. J., Kotloff, R. M., Latifpour, J., Zheng, T., Whiting, N. L., Schwalb, J. and Elias, J. A., 1994, J. Immunol. 152, 1419–1427.

What is claimed is:

1. A DNA molecule comprising the nucleotide sequence shown in SEQ ID NO:1 coding for a gene product having an anti-apoptotic effect.

2. A polypeptide having the amino acid sequence shown in SEQ ID NO:2.

* * * * *